United States Patent
Mohammad

(10) Patent No.: US 6,776,775 B1
(45) Date of Patent: Aug. 17, 2004

(54) HYPODERMIC SYRINGE NEEDLE ASSEMBLY AND METHOD OF MAKING THE SAME

(76) Inventor: Owais Mohammad, 5004 Rittenhouse St., Riverdale, MD (US) 20737

( * ) Notice: Subject to any disclaimer, the term of this patent is extended or adjusted under 35 U.S.C. 154(b) by 214 days.

(21) Appl. No.: 10/133,491

(22) Filed: Apr. 29, 2002

Related U.S. Application Data

(63) Continuation-in-part of application No. 09/613,753, filed on Jul. 11, 2000, now Pat. No. 6,669,671, which is a continuation-in-part of application No. 09/471,094, filed on Dec. 23, 1999, now Pat. No. 6,379,337.
(60) Provisional application No. 60/291,019, filed on May 16, 2001.

(51) Int. Cl.⁷ ................................................. A61M 5/32
(52) U.S. Cl. ......................... 604/195; 604/264; 604/198
(58) Field of Search ................................. 604/195, 263, 604/264, 162, 196, 198, 218, 128, 919, 181

(56) References Cited

U.S. PATENT DOCUMENTS

| | | |
|---|---|---|
| 2,927,584 A | 3/1960 | Wallace |
| 3,134,380 A | 5/1964 | Armao |
| 3,892,237 A | 7/1975 | Steiner |
| 4,416,663 A | 11/1983 | Hall |
| 4,425,120 A | 1/1984 | Sampson et al. |
| 4,564,054 A | 1/1986 | Gustavsson |
| 4,639,249 A | 1/1987 | Larson |
| 4,664,654 A | 5/1987 | Strauss |
| 4,725,267 A | 2/1988 | Vaillancourt |
| 4,735,618 A | 4/1988 | Hagen |
| 4,737,150 A | 4/1988 | Baeumle et al. |
| 4,758,231 A | 7/1988 | Haber et al. |
| 4,772,272 A | 9/1988 | McFarland |
| 4,795,432 A | 1/1989 | Karczmer |
| 4,804,371 A | 2/1989 | Vaillancourt |
| 4,816,022 A | 3/1989 | Poncy |
| 4,838,863 A | 6/1989 | Allard et al. |
| 4,842,587 A | 6/1989 | Poncy |
| 4,846,809 A | 7/1989 | Sims |
| 4,863,436 A | 9/1989 | Glick |
| 4,887,998 A | 12/1989 | Martin et al. |
| 4,900,307 A | 2/1990 | Kulli |

(List continued on next page.)

Primary Examiner—Henry Bennett
Assistant Examiner—Camtu Nguyen
(74) Attorney, Agent, or Firm—Bacon & Thomas

(57) ABSTRACT

A retractable needle assembly for use in medical procedures, comprising:
  a needle assembly including a hub, a hollow needle passing through the hub and projecting from the posterior end of the hub, and a tubular sleeve having a radially directed hole therethrough connected with the anterior end of the hub;
  a tubular sheath having a wall with a radially directed hole therethrough, wherein the needle assembly is positioned within the tubular sheath so that it may be moved reversibly between an exposed position and a retracted position;
  a means for reversibly locking the needle assembly in its exposed position;
  a means for reversibly locking the needle assembly in its retracted position; and
  a means for permanently locking the needle assembly in its retracted position, said permanent locking means comprising a radially-directed peg mounted on an exterior surface of the tubular sheath so that one end of the radially-directed peg is adapted to be pushed inwardly through the hole in the wall of the tubular sheath and through the hole in the tubular sleeve, wherein said one end of the radially-directed peg may not be withdrawn through the hole in the tubular sleeve after it has been pushed through the hole in the tubular sleeve.

46 Claims, 35 Drawing Sheets

U.S. PATENT DOCUMENTS

| | | |
|---|---|---|
| 4,900,311 A | 2/1990 | Stern et al. |
| 4,915,697 A | 4/1990 | DuPont |
| 4,917,669 A | 4/1990 | Bonaldo |
| 4,917,673 A | 4/1990 | Coplin |
| 4,923,445 A | 5/1990 | Ryan |
| 4,927,416 A | 5/1990 | Tomkiel |
| 4,929,237 A | 5/1990 | Medway |
| 4,943,282 A | 7/1990 | Page et al. |
| 4,966,592 A | 10/1990 | Burns et al. |
| 4,998,924 A | 3/1991 | Ranford |
| 5,000,740 A | 3/1991 | Ducharme et al. |
| 5,011,475 A | 4/1991 | Olson |
| RE33,585 E | 5/1991 | Haber et al. |
| 5,013,304 A | 5/1991 | Russell et al. |
| 5,086,780 A | 2/1992 | Schmitt |
| 5,088,986 A | 2/1992 | Nusbaum |
| 5,092,845 A | 3/1992 | Chang |
| 5,104,385 A | 4/1992 | Huband |
| 5,125,414 A | 6/1992 | Dysarz |
| RE34,045 E | 8/1992 | McFarland |
| 5,219,338 A | 6/1993 | Haworth |
| 5,222,947 A | 6/1993 | D'Amico |
| 5,232,456 A | 8/1993 | Gonzalez |
| 5,246,428 A | 9/1993 | Falknor |
| 5,248,301 A * | 9/1993 | Koenig, Jr. et al. ..... 604/288.02 |
| 5,254,100 A | 10/1993 | Huband |
| 5,279,579 A | 1/1994 | D'Amico |
| 5,290,255 A | 3/1994 | Vallelunga et al. |
| 5,312,359 A | 5/1994 | Wallace |
| 5,323,456 A | 6/1994 | Oprea |
| 5,411,487 A | 5/1995 | Castagna |
| 5,423,758 A | 6/1995 | Shaw |
| 5,501,675 A | 3/1996 | Erskine |
| 5,573,513 A | 11/1996 | Wozencroft |
| 5,591,138 A | 1/1997 | Vaillancourt |
| 5,685,855 A | 11/1997 | Erskine |
| 5,695,474 A | 12/1997 | Daugherty |
| 5,695,475 A | 12/1997 | Best, Jr. et al. |
| 5,769,826 A | 6/1998 | Johnson et al. |
| 5,779,679 A | 7/1998 | Shaw |
| 5,788,677 A | 8/1998 | Botich et al. |
| 5,824,001 A | 10/1998 | Erskine |
| 5,830,190 A | 11/1998 | Howell |
| 6,193,690 B1 * | 2/2001 | Dysarz ..................... 604/161 |

* cited by examiner

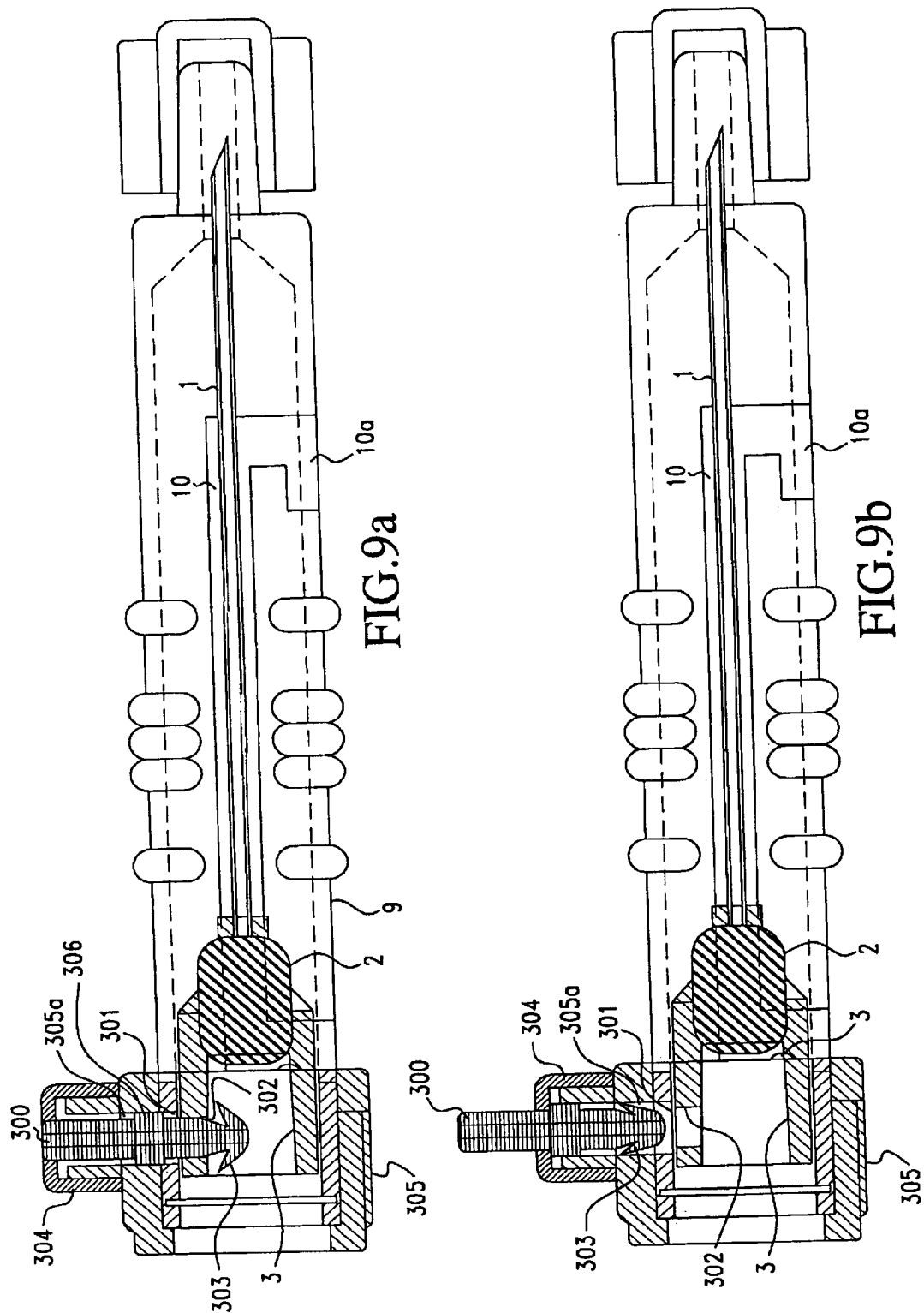

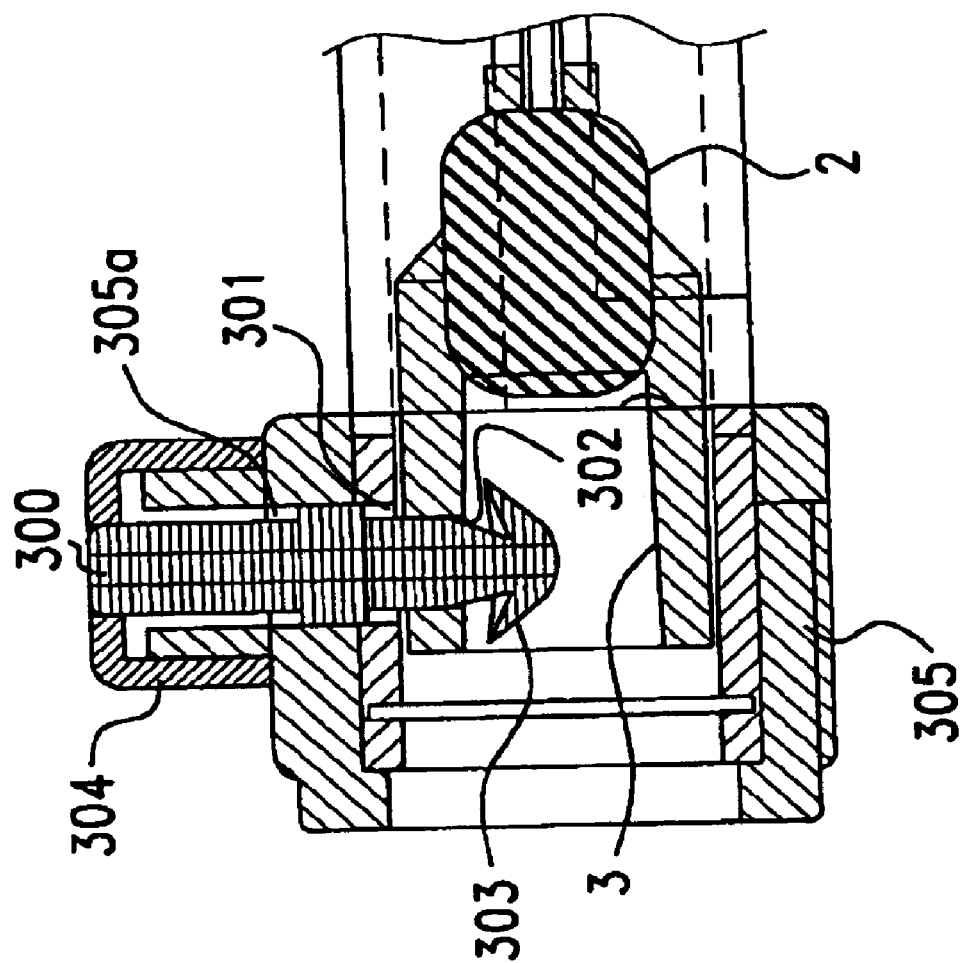

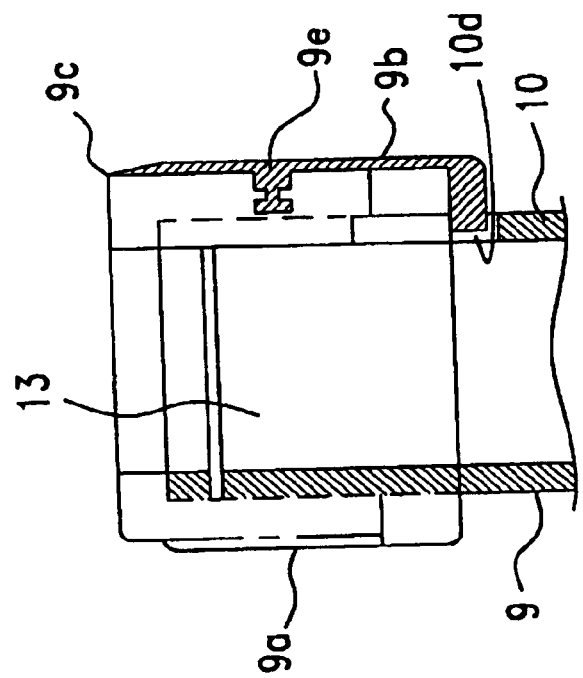
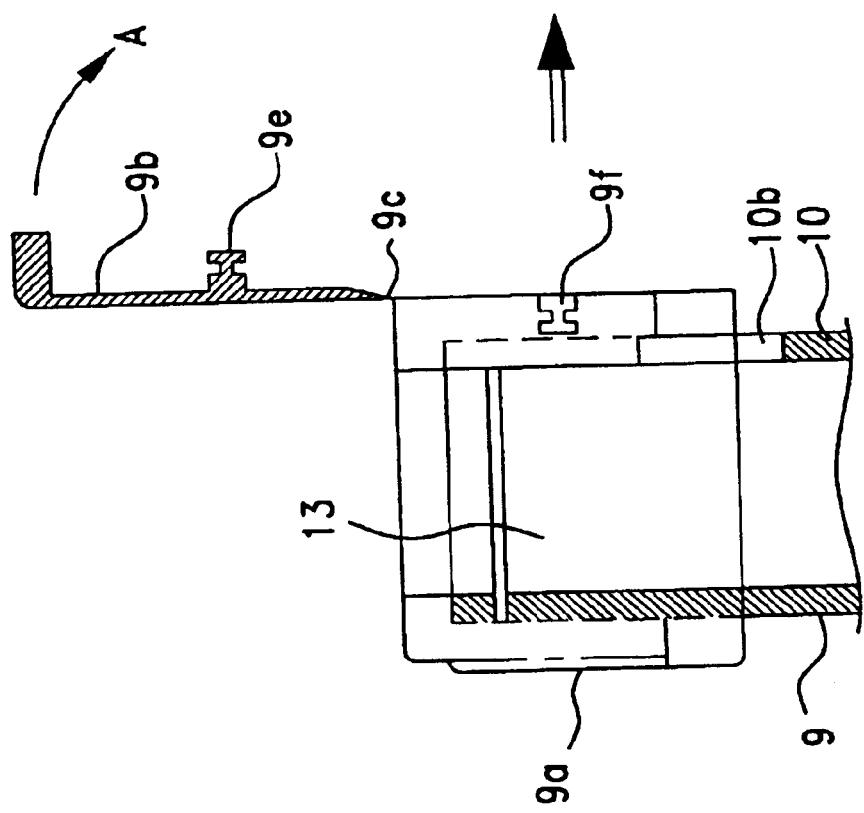
FIG.10d
FIG.10c

Grooved container in two pieces joined by threaded ends

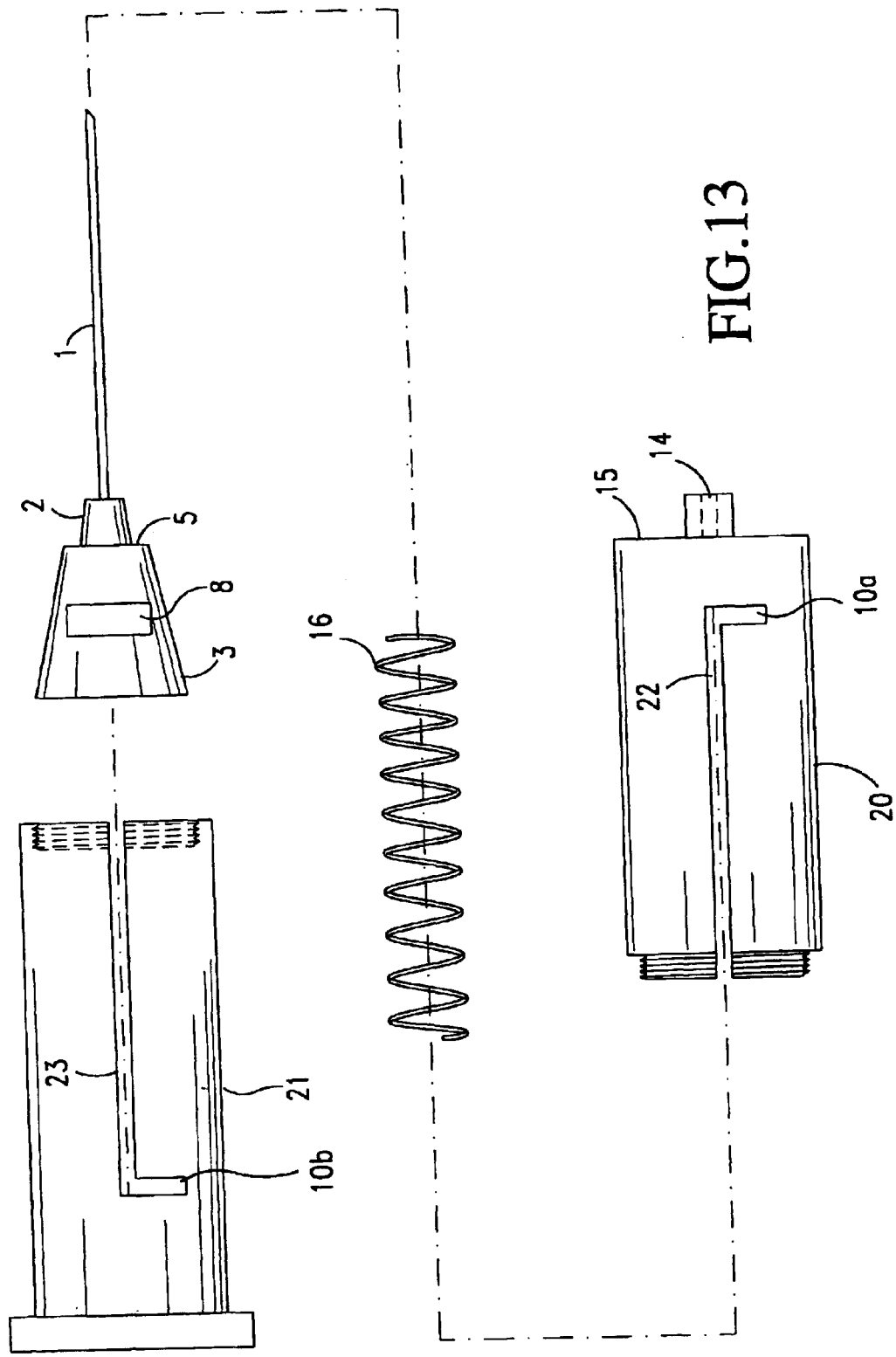

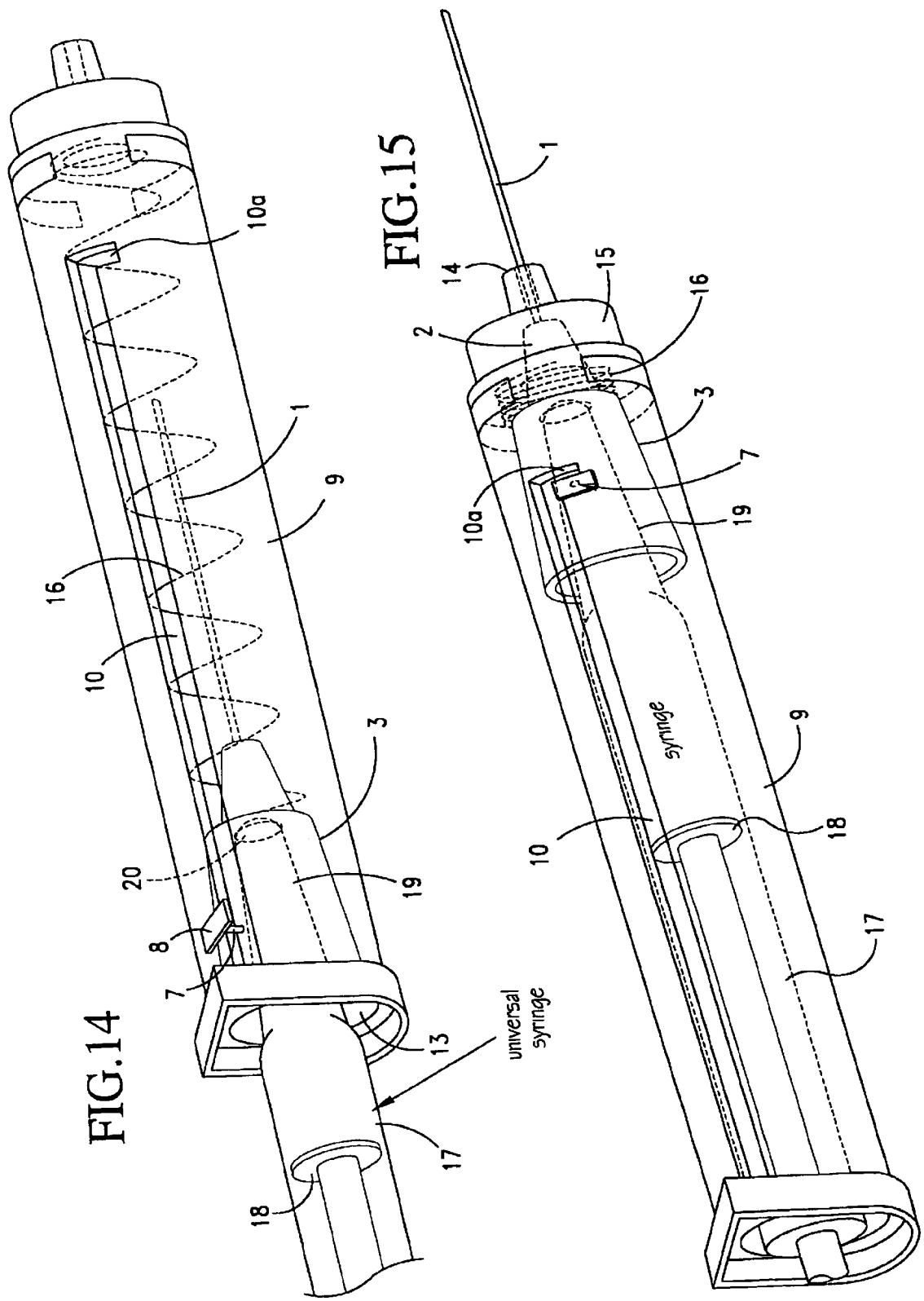

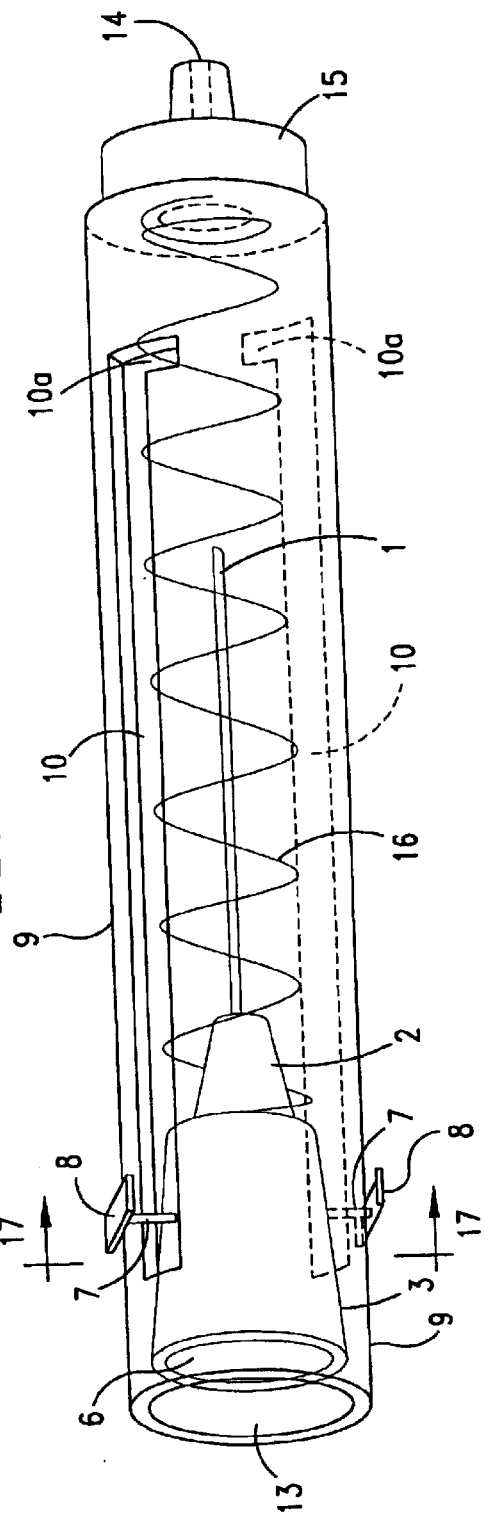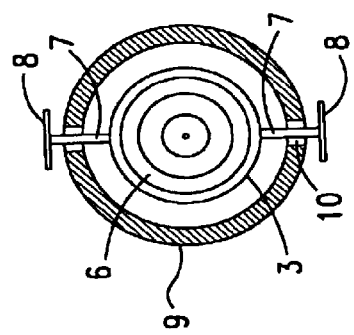

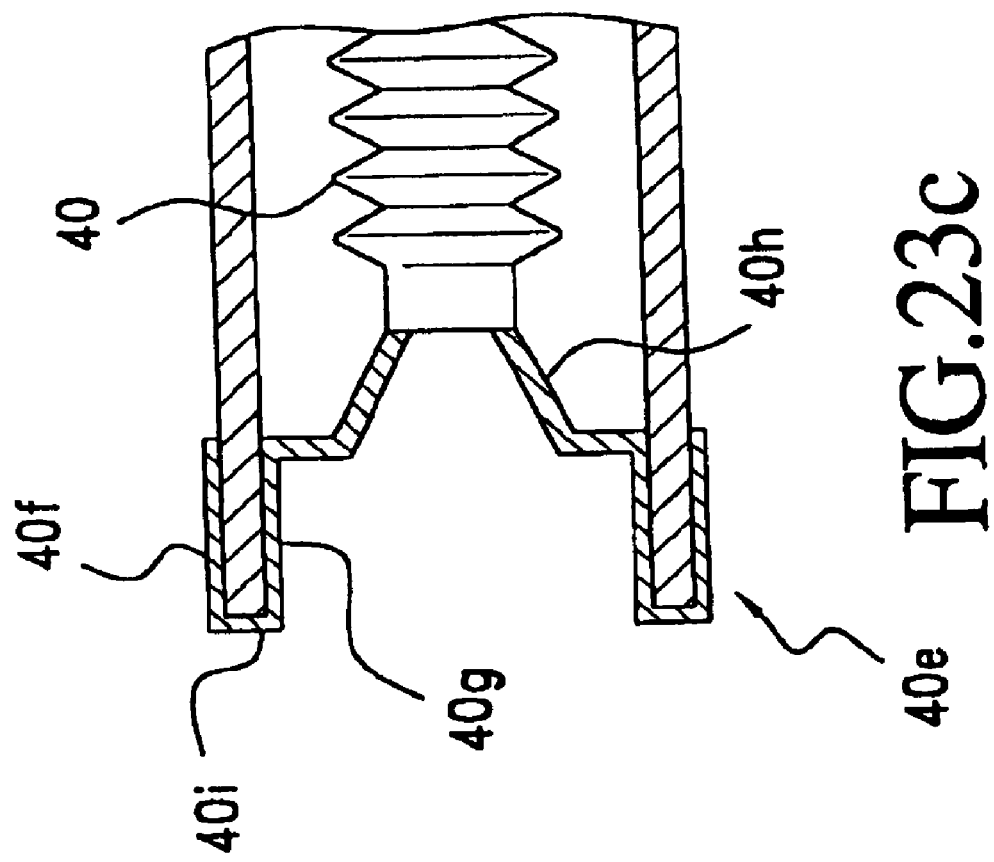

HYPODERMIC SYRINGE NEEDLE ASSEMBLY AND METHOD OF MAKING THE SAME

CONTINUATION INFORMATION

This application is a non-provisional application of U.S. provisional patent application entitled "HYPODERMIC SYRINGE ASSEMBLY AND METHOD OF MAKING THE SAME," U.S. Ser. No. 60/291,019, filed May 16, 2001, having Owais Mohammad named as inventor. The 60/291,019 application is hereby incorporated by reference in its entirety. Further, this application is a continuation-in-part of Ser. No. 09/613,753, filed Jul. 11, 2000 now U.S. Pat. No. 6,669,671, which is a continuation-in-part of Ser. No. 09/1471,094, filed Dec. 23, 1999 now U.S. Pat. No. 6,379,337. The disclosure of the applications cited above is incorporated by reference herein. Additionally, the disclosure of each of the following applications having Owais Mohammad named as inventor is incorporated by reference herein: Ser. No. 09/218,040, filed Dec. 22, 1998; and Ser. No. 09/316,047, filed May 21, 1999.

BACKGROUND OF THE INVENTION

The present invention generally refers to hypodermic syringe needles for medical use. More particularly, the invention relates to hypodermic safety needles which retract into a container when not in use, preventing unintentional contact with the needle.

Prior art injection needles feature hollow needles which extend through a plastic hub. To prevent a user from accidentally pricking himself with the point of a needle, the needle is covered with a removable cover. Such covers frictionally engage the plastic hub, and may be readily removed once the needle is attached to a syringe barrel. After use, the cover may be reattached to the needle assembly, which is then separated from the syringe barrel and discarded. However, there is an unacceptable risk of accidental injury resulting from contact with the point of the needle during the recapping step. This is particularly dangerous as biological fluids contaminating the needle could enter the user's bloodstream. An improved means of covering a used injection needle is needed.

A wide variety of needles having a means for shielding a syringe needle from accidental contact with a user's fingers have been developed. For example, U.S. Pat. No. 4,900,311, "Hypodermic Syringe", issued to Stem on Feb. 13, 1990, relates to a hypodermic syringe having a syringe barrel, an injection needle attached to the syringe barrel, and a needle guard of elliptical cross section disposed around the syringe barrel. The needle guard may be moved from a first position which covers the needle to a second position which exposes the needle. When the guard is in the second position, tabs on the interior of the guard engage slots on the syringe barrel, locking the guard into position. When the tabs are released from the slots by squeezing the elliptical guard along its longitudinal axis, a spring causes the guard to move into the first position, hiding the needle. The entire syringe assembly is then discarded.

This device, while useful, does have certain drawbacks. The syringe barrel used with this assembly has a highly specialized structure; a generic syringe barrel cannot readily be substituted. Also, the syringe barrel cannot readily be sterilized and reused. No provision for separation of the needle from the syringe barrel without removing the syringe needle from the protective needle guard is provided. Finally, there is the risk of accidentally squeezing the elliptical needle guard, causing the spring to move the needle guard into a position which conceals the needle prior to use of the needle.

U.S. Pat. No. 4,664,654, "Automatic protracting and locking hypodermic needle guard", issued to Strauss on May 12, 1987, relates to a two-piece needle shield comprising a sliding member and a stationary member. A latch holds the sliding member in position. When the latch is released, a spring causes the sliding member to retract inside the stationary member, exposing the needle. However, this device causes the user to place his hand in proximity to the needle at the time it is exposed, increasing the likelihood of injury from accidental contact with the needle.

U.S. Pat. No. 5,246,428, "Needle Safety Mechanism", issued to Falknor on Sept. 21, 1993, relates to a needle safety mechanism comprising a base adapted to be fixed with respect to the needle, and a sheath which is movable between a first position which exposes the needle and a second position which covers the needle. A latch cooperative between the base and the sheath may be used to releasably latch the sheath in the position which covers the needle. A spring biases the sheath into the needle covering position. No mechanism for latching the sheath in a position which exposes the needle is provided, however. This may be an inconvenience for workers who wish to see the precise spot where they are administering an injection.

U.S. Pat. No. 5,279,579, "Self-recapping Injection Needle Assembly", issued to D'Amico on Jan. 18, 1994, relates to a self-capping injection needle assembly which includes a hub slidably positioned within a cylindrical cover adapted to receive a syringe barrel, and a needle mounted on the hub. A spring biases the hub into a position in which the needle is contained within the tubular cover. When the spring is compressed, the hub may slide into a position which exposes the needle. The hub includes a pin which slidably engages a longitudinal groove in the tubular cover. The groove includes a transverse leg adapted to receive the pin. When the pin is positioned in the transverse leg, the hub is releasably locked into a position which exposes the needle. The hub has a threaded female joint which may be screwed onto a syringe barrel having a corresponded threaded male joint. Different size tubular covers may be used for different size syringe barrels.

This device has certain disadvantages. First, in a medical environment time is often a critical factor. A more rapid method of affixing a needle to a syringe barrel than screwing it on is desirable. Also, only syringe barrels with a specific type of joint adapted to mate with the hub are usable with this device. Most commonly used medical syringe barrels have frusto-conical tips which frictionally engage syringe needle hubs having frusto-conical cavities therein; such commonly used barrels cannot be used with the threaded connections envisioned by D'Amico. D'Amico requires that a hub having a specific diameter must be used with a tubular cover having an inner diameter which is substantially equal to the hub diameter. Most commonly available syringe needle hubs have a single standard size, and cannot be used with a range of tubular cover sizes. Therefore, D'Amico's invention necessitates creation of a range of expensive and specialized syringe needles having a range of hub sizes. Also, since the diameter of D'Amico's hub is very nearly equal to the interior diameter of the tubular cover, it is difficult to insert a hub having a protruding pin into the cover. An easy method of assembling such a device is desirable.

There is a long-felt need in the art for a safety needle assembly having a retractable needle which may be easily assembled, and which may be used with commonly available syringe barrels having frusto-conical tips which frictionally engage a syringe needle assembly. The required safety needle assembly must also avoid the other disadvantages of known prior art devices. It is an object of this invention to provide such a safety needle assembly.

SUMMARY OF THE INVENTION

The present invention provides a disposable hypodermic syringe needle which retracts into a container for safe disposal. The retractable needle assembly comprises:

a needle assembly, said needle assembly comprising a hub having an anterior end and a posterior end, a hollow needle passing through the hub and projecting from the posterior end of the hub; and a tubular sleeve connected with a peripheral edge of the hub and projecting from the anterior end of the hub, said sleeve having a radially directed hole therethrough; and a tubular sheath having a wall with a radially directed hole therethrough, an anterior end, and a posterior end, said posterior end having an opening therethrough. The needle assembly is positioned within the tubular sheath with the hollow needle being directed toward the opening in the posterior end of the sheath. The needle assembly may be moved reversibly along the axis of the sheath between an exposed position in which the hollow needle passes through the opening in the posterior end of the sheath and a retracted position in which the hollow needle is contained within the tubular sheath. The retractable needle assembly further comprises a plurality of locking mechanisms, each designed to lock the needle assembly into a specified position. The needle assembly comprises a means for reversibly locking the needle assembly in its exposed position; a means for reversibly locking the needle assembly in its retracted position; and a means for permanently locking the needle assembly in its retracted position. In one embodiment, the permanent locking means comprises a radially-directed peg mounted on an exterior surface of the tubular sheath so that one end of the radially-directed peg is adapted to be pushed inwardly through the hole in the wall of the tubular sheath and through the hole in the tubular sleeve. This end of the radially-directed peg may not be withdrawn through the hole in the tubular sleeve after it has been pushed through the hole in the tubular sleeve. Other embodiments of the permanent locking means are also feasible.

Preferably, the tubular sheath or container features a tubular wall having a longitudinal slot therethrough. One end of the container is open so that a syringe barrel may be received therein. The second, or posterior, end of the container has an opening which is sufficiently large to allow a hypodermic needle to pass therethrough, but is too small to allow the hub or a syringe barrel to pass therethrough. A spring may engage the hub of the needle assembly and a ridge on the interior of the wall of the second end of the container. This spring biases the hub away from the second end of the container so that the needle attached to the hub is hidden within the container. When the spring is compressed, the needle is able to pass through the opening of the posterior end of the container. A pin attached to the annular sleeve is slidably engaged by the longitudinal slot in the container wall, holding the needle within the container while allowing it to slide back and forth. A knob mounted on the pin is positioned outside the container. The knob is too large to pass through the longitudinal slot, and acts to position the hub of the needle along the axis of the container. When the knob is pushed toward the second end of the container, the hub moves toward the second end of the container, compressing the spring and causing the needle to emerge through the second open end of the container. A means for reversibly engaging the knob when the spring is compressed is also provided. This allows the needle to be retained in an exposed position.

The needle may be frictionally secured to a syringe barrel having a plunger slidably mounted therein. More specifically, a syringe barrel having a tip is secured to the needle assembly by inserting the tip of the syringe barrel into the cavity of the annular sleeve until the barrel tip is frictionally secured to the barrel sleeve. Additional features of the invention will be described in the detailed description of the preferred embodiments. Any syringe barrel having an appropriately shaped tip may be used with the inventive needle assembly.

Other embodiments of this invention are contemplated. The needle assembly of this invention may be attached to an IV tube and used for intravenous administration of fluids. Also, a modified needle assembly having a double-ended hypodermic needle that is affixed to a hub may be used to withdraw samples of venous blood.

DESCRIPTION OF THE DRAWINGS

FIG. 1e illustrates an end view of the needle assembly of FIG. 1a.

FIGS. 2 and 3 show grooved containers designed to contain the needle of FIG. 1a.

FIGS. 7, 8a, 8b, 8c, 9a, 9b, 9c, 9d, 9e, 9f, 10a, 10b, 10c and 10d show mechanisms to irreversibly lock a retractable needle in a retracted configuration.

FIG. 13 is an exploded view of the retractable hypodermic safety needle within a container shown in FIG. 12.

FIGS. 14 and 15 show a modified version of the apparatus of FIG. 4.

FIGS. 16 and 17 show a second modified version of the apparatus of FIG. 4.

FIG. 22, 22a, 23a, 23b, 23c, 25c, and 25d show a needle assembly featuring an adjustable-length tube.

DETAILED DESCRIPTION

The needle used in the present invention is designed for use with a syringe comprising a plunger and a syringe barrel having a tubular wall with a defined outer diameter, where the barrel has an open end adapted to receive the plunger and a closed end having a cylindrically symmetric tip projecting therefrom. The tip of the barrel has a defined diameter which is less than the defined outer diameter of the syringe barrel and a longitudinal bore passing through the tip and the closed end of the barrel.

Figure 1A:
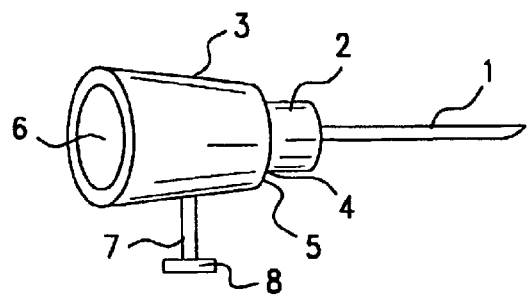
FIG. 1a illustrates a side view of a preferred needle assembly for use in the syringe assembly of this invention.
Figure 1B:
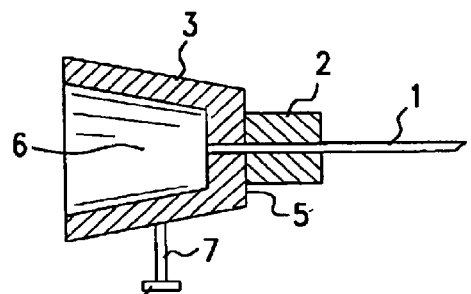
FIGS. 1b, 1c, and 1d illustrate cross-sectional views of preferred needle assembly.
Figure 1C:
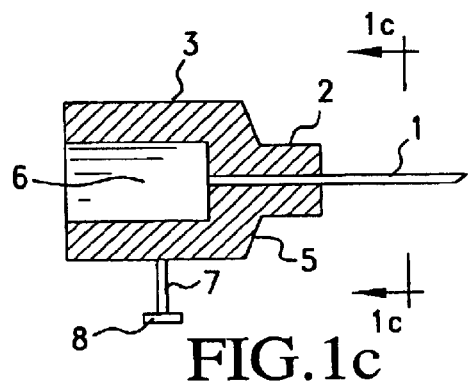
Figure 1D:
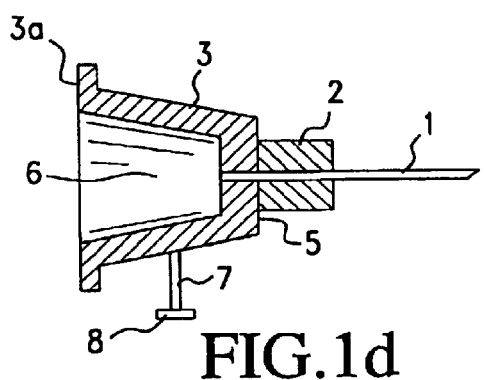

FIG. 1a illustrates a hypodermic needle for use in the syringe assembly of this invention. Needle 1 is affixed to hub 2. A hollow bore runs longitudinally through needle 1 and hub 2. An annular sleeve 3 is affixed to the outer periphery 4 of hub 2. A ledge 5 encircling hub 2 is defined by the edge of sleeve 3. Sleeve 3 defines a cavity 6 adapted to frictionally engage the tip of the syringe barrel, as shown in the cross-sectional views of FIGS. 1b and 1c. The diameter of cavity 6 is sized to match the diameter of the tip of the syringe barrel, while being substantially smaller than the diameter of the outer diameter of the tubular wall of the syringe barrel, allowing the cavity 6 to fit over the syringe barrel tip without extending over the external surface of the wall of the syringe barrel. In one preferred embodiment, the interior surface of the sleeve defines a frusto-conical cavity 6, where the sleeve is adapted to frictionally engage a frusto-conical tip of a syringe barrel (FIG. 1b). In another preferred embodiment, the interior surface of the sleeve defines a cylindrical cavity of constant diameter, where the sleeve is adapted to frictionally engage a cylindrical syringe barrel tip of constant diameter (FIG. 1c). Alternatively, the interior surface of the tubular sleeve may be threaded, allowing it to engage a threaded male joint on the syringe barrel. If desired, the exterior surface of the tubular sleeve may be threaded, allowing it to engage a threaded female joint on the syringe barrel. Finally, the user may wish to connect the needle to a syringe barrel having a Luer-Loc® connector. Such a connector typically includes a threaded female joint on the syringe barrel, surrounding a non-threaded male joint on the syringe barrel. The interior surface of the tubular sleeve frictionally engages the inner male joint on the Luer-Loc® connector on the syringe barrel, while a flange 3a on the exterior surface of the tubular sleeve engages the threaded female joint on the syringe barrel, as shown in FIG. 1d.

Figure 1E:
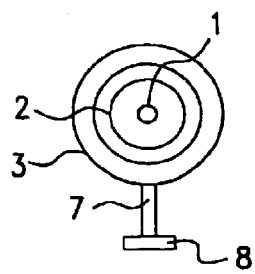

A radially projecting member 7 is affixed to the outer surface of sleeve 3. A thumbrest, knob or crosspiece 8 is mounted on member 7. Member 7 commonly takes the form of a pin having a round cross section; however, other configurations are possible. Member 7 may have a square, rectangular, or oval cross section. If desired, 7 may have a length which is substantially greater than its width. The crosspiece may take any of several forms. It may be square. It may also be a round disk, a spherical knob, or a hemispherical knob. It may also take the form of a ring which encircles hub 2, without being connected to hub 2, except by means of stem 7. Crosspiece 8 should be positioned so that, when viewed along the axis of needle 1, piece 8 and pin 7 intersect at a right angle (FIG. 1e). Although pin 7 and crosspiece 8 may be manufactured separately and secured together, it is preferred that 7 and 8 be manufactured as a single piece.

Figure 2:
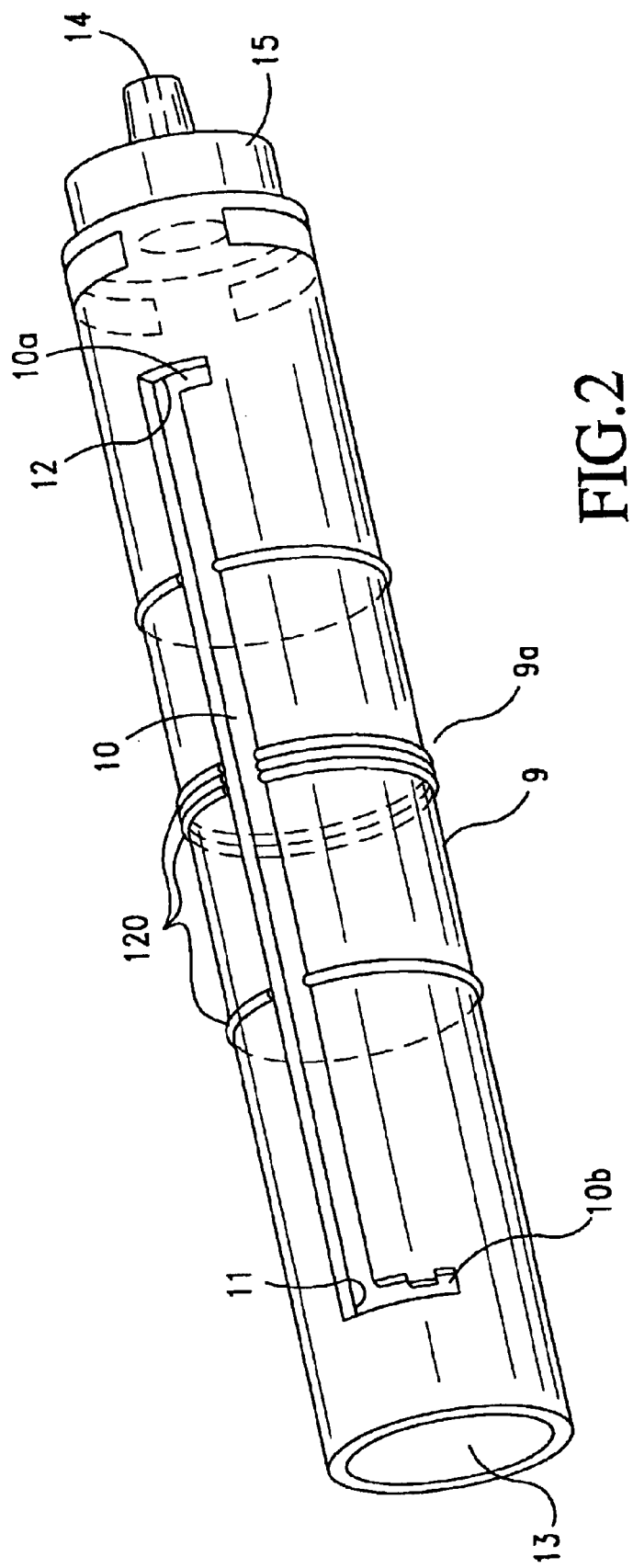
Figure 3:
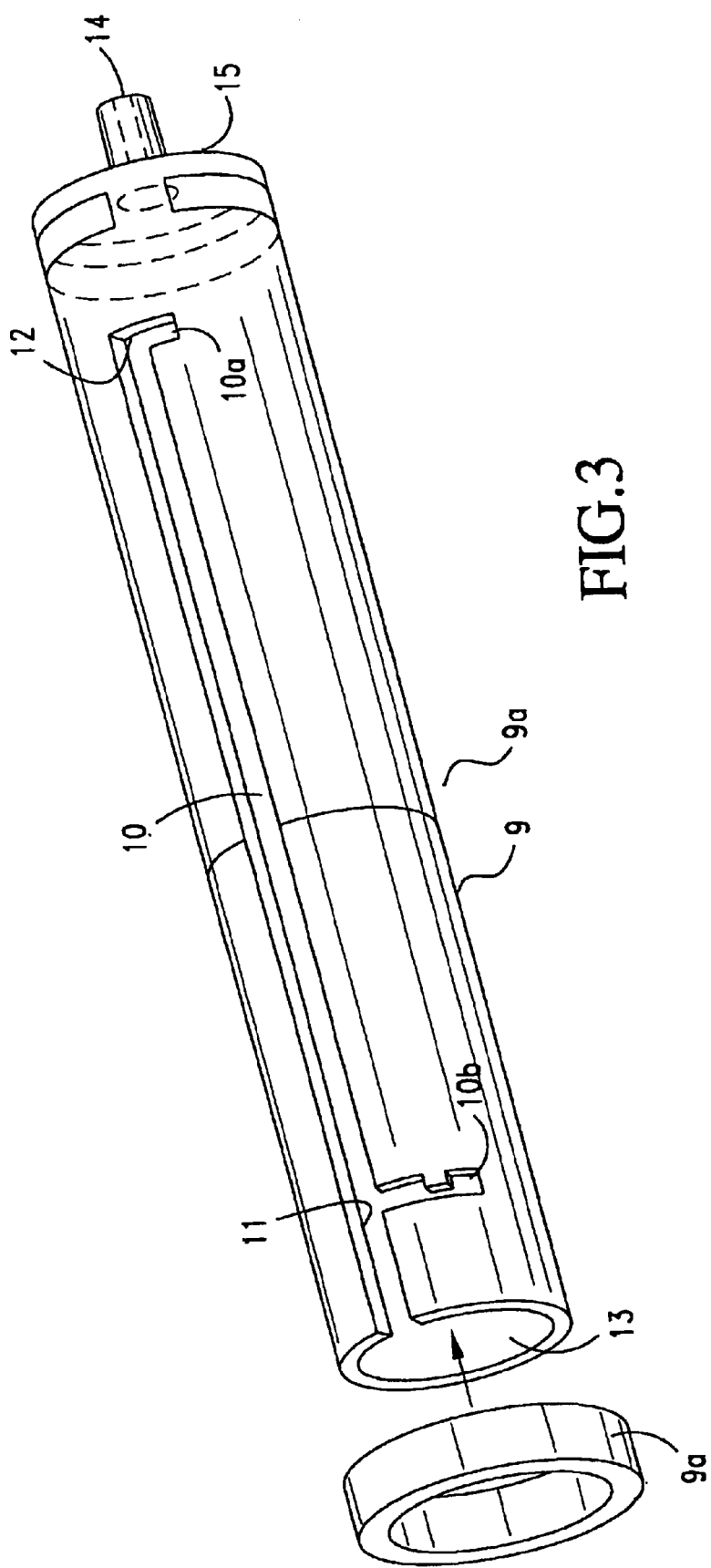

FIG. 2 shows a grooved container designed to house the needle of FIG. 1a. The container has a tubular wall 9 having a longitudinal slot 10 therethrough. A first end of the container has an opening 13 adapted to receive a syringe barrel. The second end of the container has an opening 14 which is large enough to allow needle 1 to pass therethrough, but too small to admit a syringe barrel or a human finger. A ledge 15 on the second end of the container runs from the interior of wall 9 to the edge of opening 14. Slot 10 runs from a point near the first end of the container, without reaching the first end of the container, to a point near the second end of the container, without reaching the second end of the container. A second slot 10a, running a part of the way around the circumference of wall 9, intersects slot 10 near the second end of the container. A similar slot 10b intersects slot 10 near the first end of the container. Slots 10a and 10b are preferably parallel to each other. A series of circumferential ridges 120 may optionally be positioned on the exterior of the container, said ridges being effective to strengthen the container, although this feature is not necessary for proper function of the invention. Slots 10a and 10b are preferably L-shaped slots, as shown in FIG. 2, or straight slots, as shown in FIG. 3. The slots 10a and 10b may have one or more teeth 200.

Figure 20:
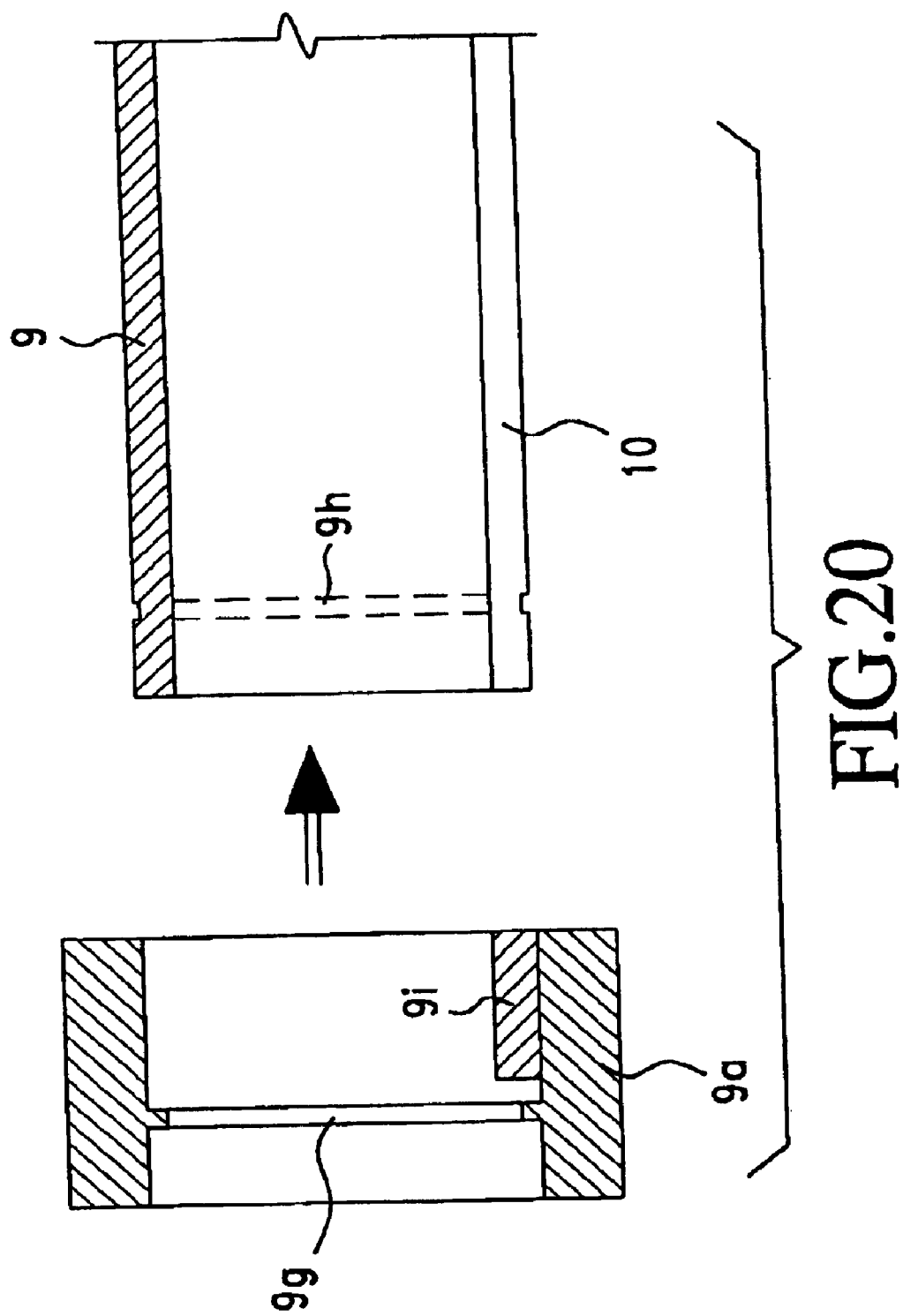
FIG. 20 shows how rigid ring 9a fits onto the tubular container of FIG. 2.

Although the container may be made in a single piece, it is preferred to manufacture the container in two pieces (FIG. 3). The first piece is a housing or a container having a tubular wall 9 with a longitudinal slot 10 therethrough, exactly as previously described; the sole difference is that the longitudinal slot 10 extends from the first open end of the container to a defmed point near the second open end of the container, slot 10 being open-ended at the first open end of the container and closed at the second open end of the container discuss slots 10a & 10b. The second piece of the container is a rigid ring 9a having a first end and a second end, where the rigid ring 9a is positioned over the first open end of the container so as to close the open end of the longitudinal slot. Preferably, one end of the ring is flush with one edge of slot 10b without blocking slot 10b. To help hold the ring 9a in position on the wall 9 of the first piece of the container, the ring has a circumferential ridge on its interior surface, and the container has a circumferential groove on its exterior surface near the first open end of the container (FIG. 20). The rigid ring fits over the first open end of the container until the circumferential ridge snaps into the circumferential groove. Additionally, the rigid ring may have a longitudinal ridge on its interior surface, where the longitudinal ridge fits into the open end of the longitudinal slot so as to prevent the ring from rotating relative to the wall 9.

Figure 4:
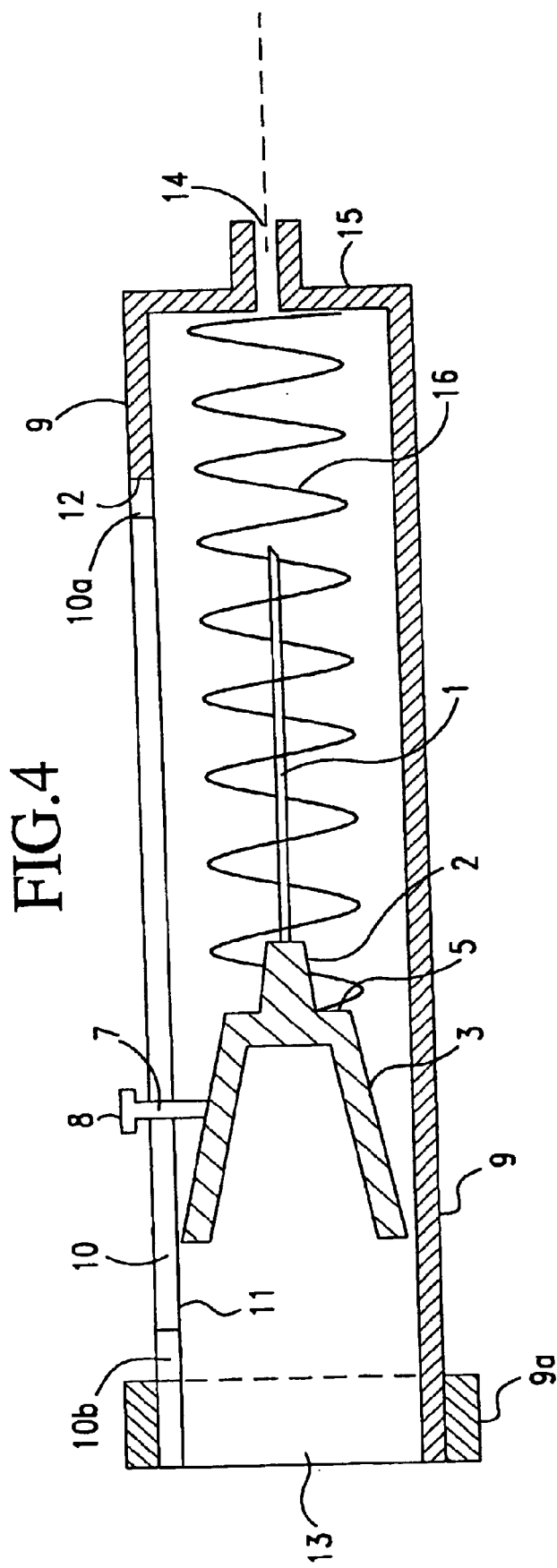
FIG. 4 shows a retractable hypodermic safety needle within a container, with the needle in a retracted configuration.

FIG. 4 shows how the needle assembly of FIG. 1a is contained within the container of FIG. 2. The needle assembly is positioned within the container with pin 7 slidably engaging slot 10. Crosspiece 8 helps to retain pin 7 within slot 10. Piece 8 is sufficiently large that it cannot pass through slot 10 into the interior of the container, and is rigidly secured to a defined position along the length of pin 7, where the defmed position on pin 7 is chosen so that hub 2 of the needle assembly is positioned along the cylindrical axis of the container, as shown in the cross-sectional view of FIG. 4. More particularly, the distance between the axis of hypodermic needle 1 and crosspiece 8 is equal to the one half the external diameter of the wall 9 of the container. This retains needle 1 along the axis of the container. Removal of knob 8 would allow pin 7 to slip out of slot 10, causing hub 2 to fall against the inside of wall 9. Ring 9a prevents pin 7 from exiting the open end of slot 10. As shown in FIG. 4, 9a is flush with one edge of slot 10a. In general, the size of the container can be chosen so as to accommodate any size syringe. Thus, if a large syringe is to be used, a container having a large interior diameter is required. The maximum diameter of the combination of hub 2 and sleeve 3 can be selected so as to correspond to the interior diameter of the container wall 9. Thus, a specific needle-holding assembly having a specific hub size may be manufactured for each commonly used syringe size. Alternatively, a standard-sized hub and sleeve may be used in each case, regardless of the size of the syringe and/or container. This may be done by varying the length of pin 7, so as to match the distance between sleeve 3 and the wall 9 of the container.

A needle having a hub of any desired size may be used in a container having any desired radius without losing the desired axial orientation of needle 1 by simply changing the distance between the axis of needle 1 and crosspiece 8. This makes it unnecessary to manufacture a wide variety of needle hubs, with each needle hub being reserved for a different container size, as required by D'Amico.

A spring 16 is also positioned within the container, as shown in FIG. 4. A first end of spring 16 engages ledge 15 at the second end of container 1, while the second end of spring 16 engages ledge 5 encircling hub 2. The spring acts to bias hub 2 away from the second end of the container so that needle 1 is effectively concealed within the container. This allows the user to effectively handle the assembly without pricking his fingers. Preferably, the tip of the needle bore is positioned inside 14 (FIG. 4).

Figure 5:
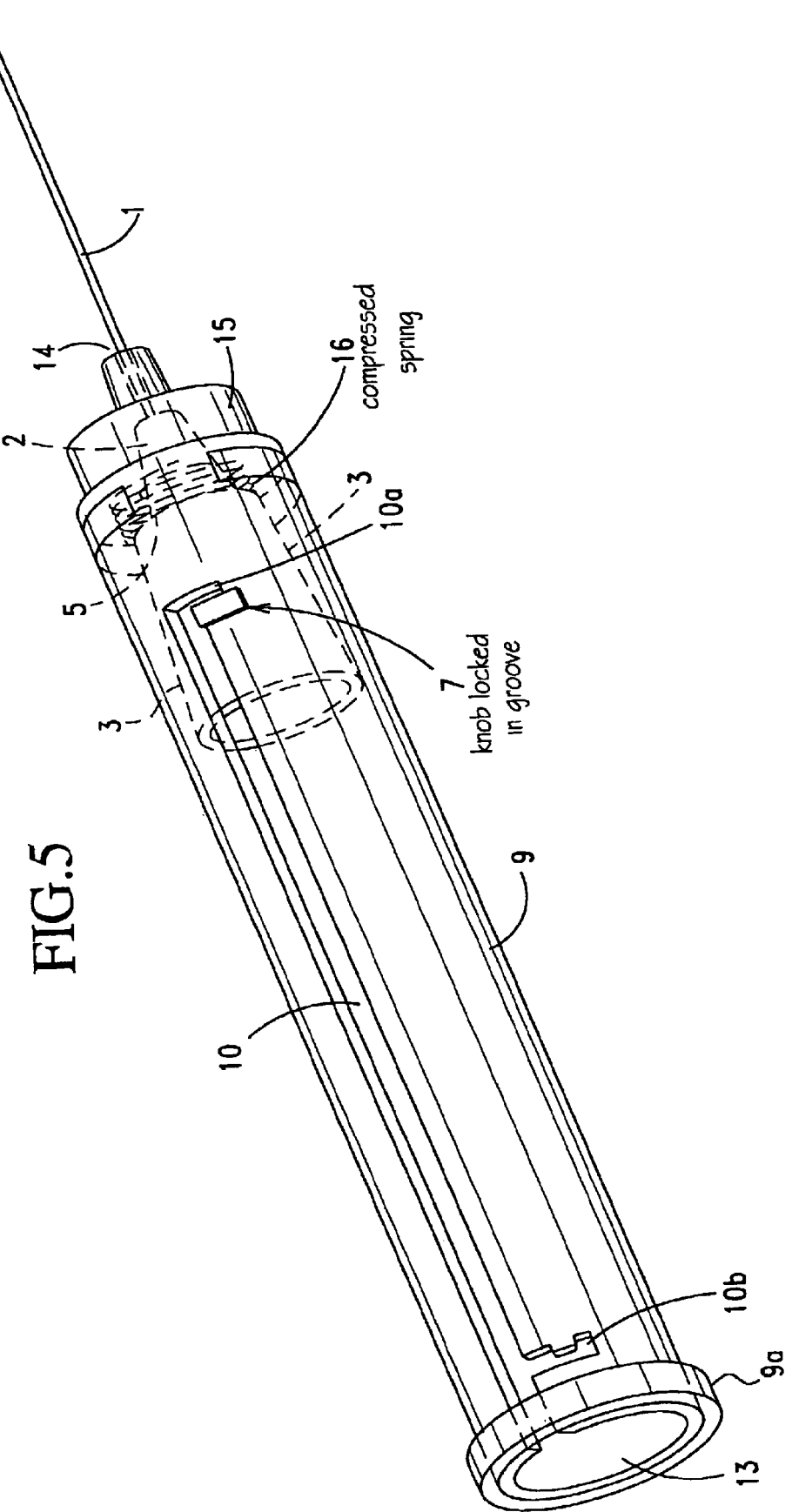
FIG. 5 shows a retractable hypodermic safety needle within a container, with the needle in an exposed configuration.

When one is ready to use the needle, needle 1 may be exposed by pushing hub 2 toward the second end of the container. This is most easily done by manually sliding crosspiece 8, attached to pin 7, along slot 10 with the user's thumb or finger. As hub 2 approaches the second end of the container, spring 16 is compressed and needle 1 passes through opening 14 in the container and is exposed. Since needle 1 is directed along the axis of the container, it is very easy to direct the needle through opening 14. When pin 7 reaches end 12 of slot 10, the needle is rotated by reversibly pushing pin 7 into slot 10a. Slot 10a acts as a stop, preventing spring 16 from decompressing and causing needle 1 to retract into the container. An illustration of the needle assembly in this configuration is shown in FIG. 5. This has the great advantage that one may expose a sheathed needle without having to position one's fingers near the needle itself, as is done when exposing the sheathed needle described by Strauss (vide supra). When it is desired to retract the needle, 16 reversibly pushes pin 7 along slot 10 pin 7 out of slot 10a, and then spring.

Figure 6C:
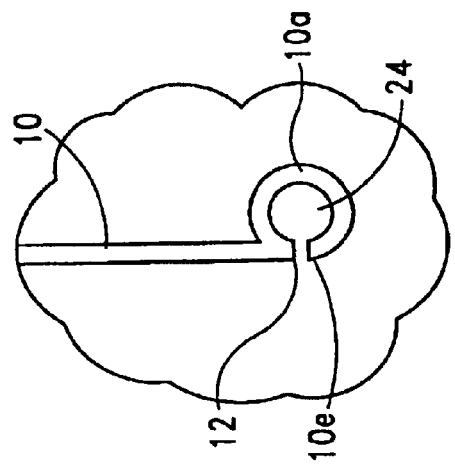
FIGS. 6a through 6g show various embodiments of locking mechanisms to hold a retractable needle in an exposed configuration.
Figure 6B:
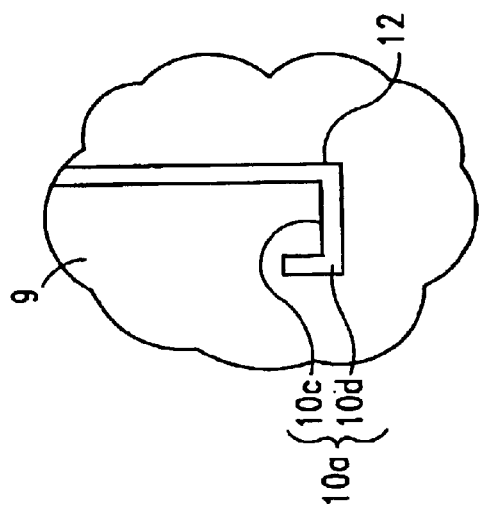
Figure 6A:
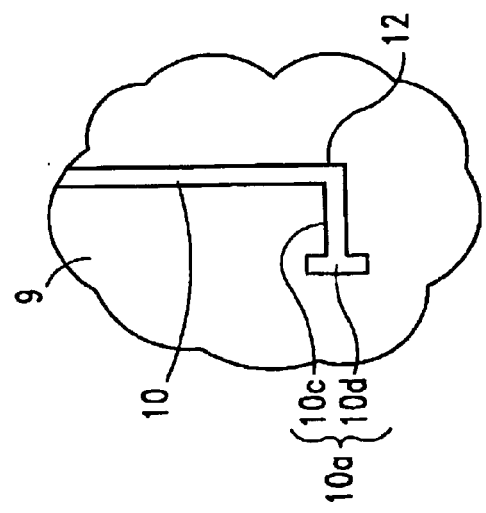

As shown in FIGS. 1 through 5, slot 10a is a simple transverse slot which intersects slot 10 at a right angle. While this is an effective arrangement, other configurations of slot 10a are possible. Three such arrangements are shown in FIGS. 6a through 6c. In FIG. 6a, slot 10a is configured as a T-shaped notch. This T-shaped notch comprises a first transverse leg 10d which intersects slot 10, and a second leg 10e which intersects the transverse leg and is substantially parallel to slot 10. If desired, transverse leg 10d and leg 10e may be configured as an L-shaped notch, as shown in FIG. 6b. The notches of FIGS. 6a and 6b operate in the following manner. Hub 2 is moved forward within the container until pin 7 reaches end 12 of slot 10. At this point, the needle is rotated by pushing pin 7 into transverse leg 10d of slot 10a until the pin reaches the point where legs 10d and 10e intersect. At this point, spring 16 biases the hub 2 away from ridge 15, causing pin 7 to enter leg 10e of slot 10a. Leg 10e acts as a stop, preventing spring 16 from decompressing further and causing needle 1 to retract into the container. Leg 10e also prevents the user from accidentally pushing pin 7 out of slot 10a.

In FIG. 6c, slot 10a is configured as a C-shaped slot, where a first end of the C-shaped slot intersects slot 10 at point 12, and a second end 10d lies in line with slot 10. The end of slot 10 is separated from the second end of slot 10a by tab 24. The C-shaped configuration of slot 10a operates in the following manner. Hub 2 is moved forward within the container until pin 7 reaches end 12 of slot 10. At this point, the needle is rotated by pushing pin 7 along slot 10a until it reaches end 10d. At this point, spring 16 biases the hub 2 away from ridge 15, pressing pin 7 against tab 24. Tab 24 acts as a stop, preventing spring 16 from decompressing further and causing needle 1 to retract into the container.

Notch 10b, which intersects longitudinal slot 10 near the first end of the container, also functions as a locking mechanism. When the needle is retracted into the container, pin 7 is adjacent to slot 10b. Pin 7 may then be pushed sideways into slot 10b so as to hold the needle assembly in the retracted position. Like slot 10a, slot 10b may be a straight transverse slot, a C-shaped slot, an L-shaped slot, or a T-shaped slot. Notches 10a and 10b are each wide enough to receive the pin engaged by the longitudinal slot. To retain pin 7 in notch 10a or in notch 10b when the needle is in use, each notch may be provided with teeth 200 which are spaced sufficiently closely together that the pin may not be pushed into, or out of, the notch without the deliberate application of force. A pair of such teeth are shown in the entrance to notch 10b in FIG. 7.

Figure 6E:
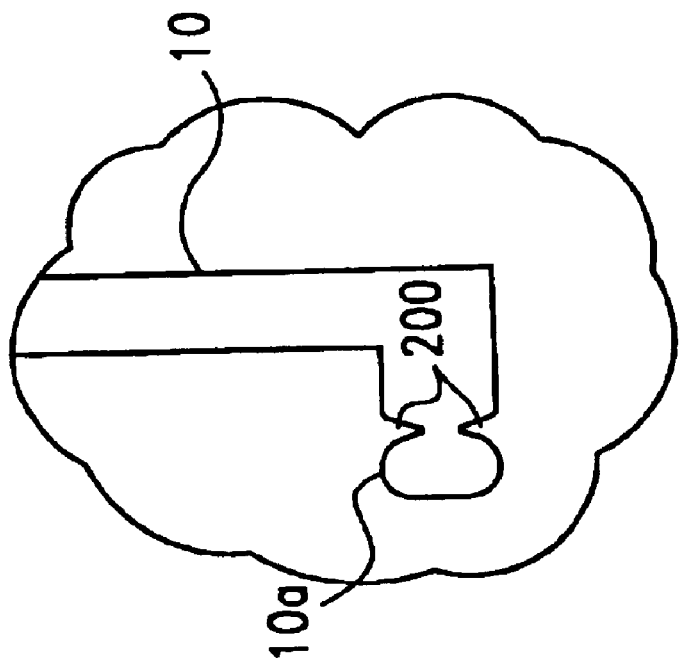
Figure 6D:
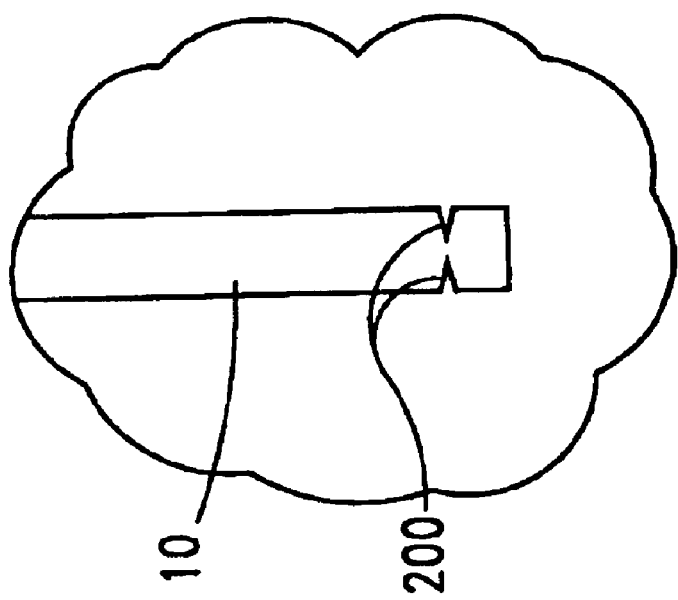

As shown in FIG. 6d, the means for reversibly locking the needle assembly in its exposed position may comprises a pair of teeth 200 on opposite sides of the longitudinal slot, said pair of teeth being positioned near a posterior end of the tubular sheath. No intersecting slots are required. A locking position is defined between the teeth and the posterior end of the longitudinal slot. The teeth cause the width of the slot to narrow to a width which is smaller than the diameter of the radially projecting member, but large enough to allow a user to push the radially projecting member through the teeth. A similar mechanism for reversibly locking the needle assembly in its retracted position comprises a pair of teeth on opposite sides of the longitudinal slot, said pair of teeth being positioned near an anterior end of the tubular sheath. Alternatively (FIG. 6e), teeth 200 may be positioned on opposite sides of a slot 10a which intersects slot 10 at a right angle.

Figure 6G:
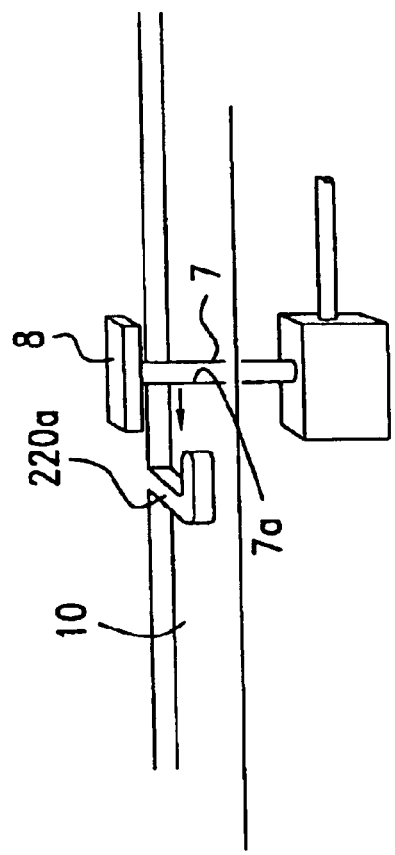
Figure 6F:
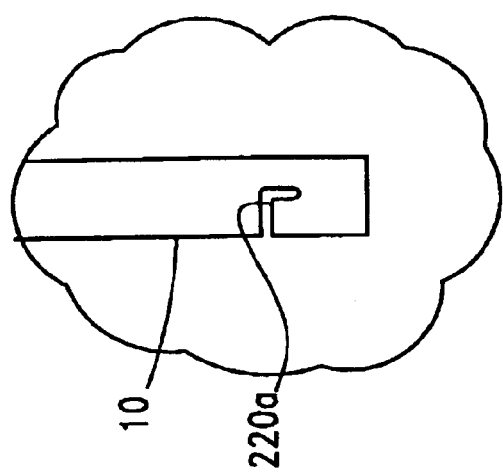

As shown in FIG. 6f, the means for reversibly locking the needle assembly in its exposed position may comprises a first hook 220a which engages the radially projecting member 7, and the means for reversibly locking the needle assembly in its retracted position may comprise a second hook 220b (not shown in FIG. 6f) which engages the radially projecting member. The first hook is located at the posterior end of the longitudinal slot, and the second hook is located at the anterior end of the longitudinal slot. If radially projecting member 7 is substantially longer than it is wide (FIG. 6g), a notch 7a in an edge of member 7 may be used to assist in engaging a hook 220*a* or 220*b*. The hook fits into the notch 7*a*, stabilizing the position of the radially projecting member.

Figure 7:
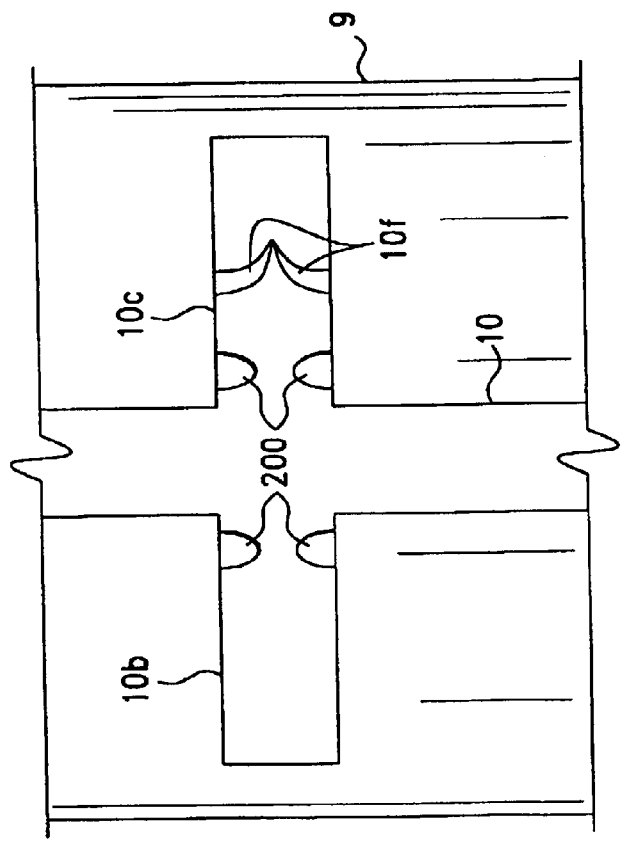

Preferably, since used syringe needles may be biohazards, the retractable syringe needle also includes a mechanism for irreversibly engaging the pin near the first end of the container so as to retain a used needle in the retracted position. One version of the irreversible locking mechanism comprises a third notch 10*c* which intersects longitudinal slot 10 so that slots 10*b* and 10*c* are collinear, extending from opposite sides of slot 10 (FIG. 7). Slot 10*c* is wide enough to receive the pin engaged by the longitudinal slot, and comprises a pair of flexible projections 10*f* extending from opposite sides of slot 10*c*. The projections have tips which contact each other, said tips being adapted to allow the pin engaged by the slot to pass therethrough when the pin enters the slot 10*c* from longitudinal slot 10, and to not allow the pin to pass therethrough to exit slot 10*c*. Each of the flexible projections makes an acute angle with the wall of slot 10*c*, and each of the flexible projections is directed away from the longitudinal slot 10. The pin 7 can pass between the projections as it enters slot 10*c* (FIG. 8*b*), but it cannot exit slot 10*c* between the projections (FIG. 8*c*). Projections 10*f* are able to bend away from slot 10 so as to allow pin 7 to pass therethrough and enter 10*c*, but they cannot bend toward slot 10 so as to allow pin 7 to exit 10*c*. If desired, one or more teeth 200 may be positioned in notch 10*c* between the opening to notch 10*c* and projections 10*f*, although they are not required for proper functioning of the retractable syringe. Teeth 200, if present, are designed so that the pin may be reversibly pushed into notch 10*c* through the deliberate application of a force having at least a first defined magnitude. The projections 10*f* are preferably designed so that force of the first defined magnitude $F_1$ is insufficient to force pin 7 through projections 10*f*. Force of a second defined magnitude $F_2$, greater than the first defined magnitude, is required to force pin 7 through projections 10*f*. Thus, the pin may be reversibly locked into notch 10*c* by pushing it into notch 10*c* with a force F, where $F_1 \leq F < F_2$; and the pin may be irreversibly locked into notch 10*c* by pushing it into notch 10*c* with a force of $F_2$ or greater. It is possible to omit notch 10*b* from the container structure entirely, and use notch 10*c* for both reversibly and irreversibly locking pin 7 into position. This is, however, much preferred to use notches 10*b* and 10*c* as separate locking mechanisms, due to the possibility of unintentionally irreversibly locking pin 7 into notch 10*c* when attempting to use notch 10*c* as a reversible lock.

Figure 9D:
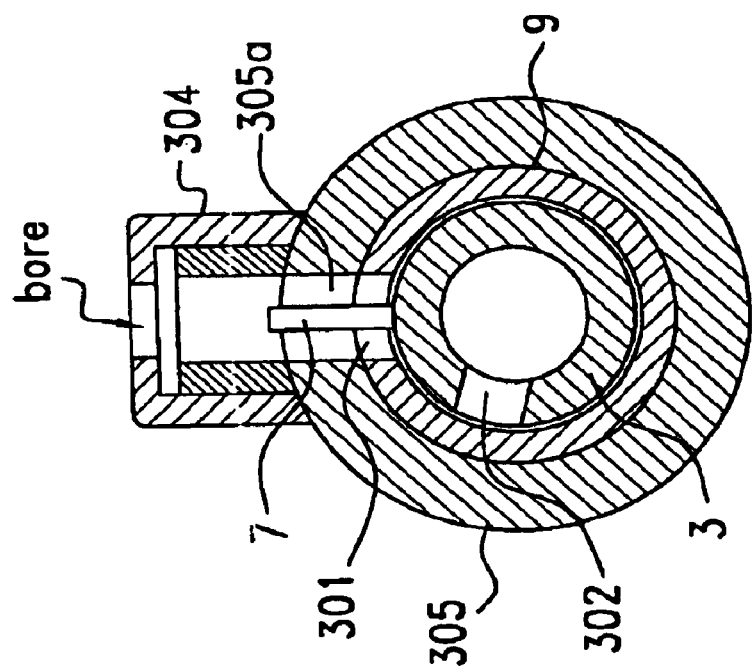
Figure 9C:
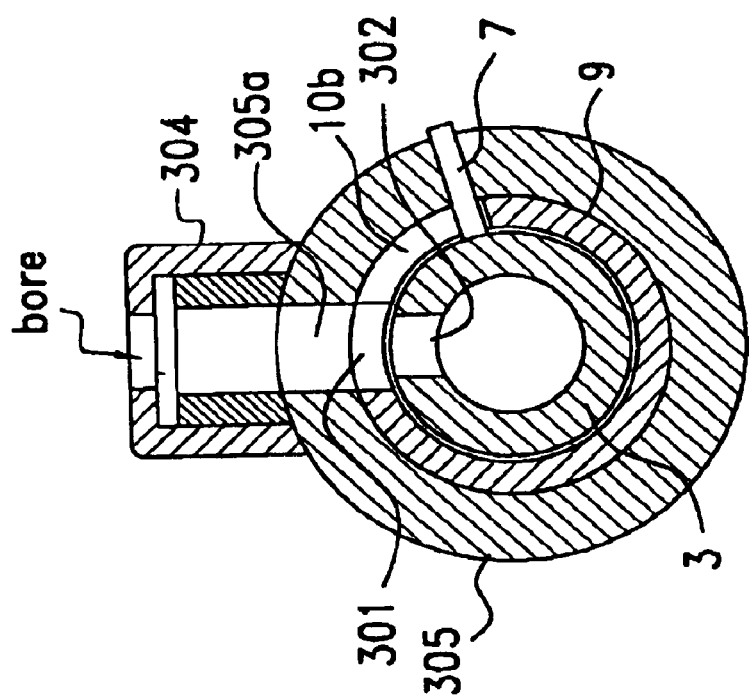

A second version of the mechanism for irreversibly engaging the pin in its retracted position, shown in FIGS. 9*a* and 9*b*, comprises a radially-directed peg 300, said radially-directed peg being mounted on an exterior surface of the tubular sheath 9 so that one end of the radially-directed peg is adapted to be pushed inwardly through a hole 301 in the wall of the tubular sheath and through a hole 302 in the tubular sleeve 3. The radially directed peg may be mounted to the tubular sheath by means of a tubular mount 304 having a bore with a diameter that corresponds to the maximum outer diameter of peg 300 so that peg 300 slides axially within mount 304. Mount 304 is mounted to the side of sheath 9 so that the axis of the bore of the mount is normal to the axis of sheath 9, and so that the bore of mount 304 is positioned above hole 301 in sheath 9. Mount 304 may be secured to sheath 10 directly, or by means of a cap 305, as shown in FIGS. 9*a* and 9*b*. Cap 305 has a hole 305*a* therethrough, with this hole being in line with holes 301 in the tubular sheath. When pin 7 enters slot 10*b* and reversibly secures the needle assembly in a retracted position, hole 302 through the tubular sleeve in the needle assembly is brought into alignment with holes 305*a* and 301 (FIG. 9*c*; peg 300 omitted for clarity). Thus, after reversibly locking the needle in its retracted position, peg 300 can be simultaneously pushed through holes 305*a*, 301, and 302, preventing movement of hub 2 relative to sheath 9. If the needle has not been reversibly locked, hole 302 is not aligned with holes 305*a* and 301, preventing peg 300 from engaging hole 302 in the tubular sleeve (FIG. 9*d*; peg 300 omitted for clarity). Holes 305*a* and 301 may have a larger diameter than hole 302. Preferably, a stop 306 on peg 300 limits the depth to which peg 300 can enter sleeve 3. The outer diameter of stop 306 is greater than the diameter of hole 302. After the end of the radially-directed peg 300 is pushed through hole 302, peg 300 may not be withdrawn through the hole in the tubular sleeve. This is due to flexible projection or projections 303, which project radially from peg 300. Projections 303 are angled toward stop 306, and away from the axis of sheath 9. Before peg 300 is pushed through holes 305*a*, 301, and 302 (FIG. 9*b*, the unlocked configuration), projections 303 are restrained to lie against peg 300 by the wall of mount 204. After peg 300 is pushed through hole 302 (FIG. 9*a*, the locked configuration), projections 303 are no longer restrained and extend radially. Since they are angled toward the interior of the wall of sleeve 3, projections 303 cannot be readily be folded away from the wall of sleeve 3. This makes it difficult or impossible to withdraw peg 300, resulting in a permanent lock.

Figure 9F:
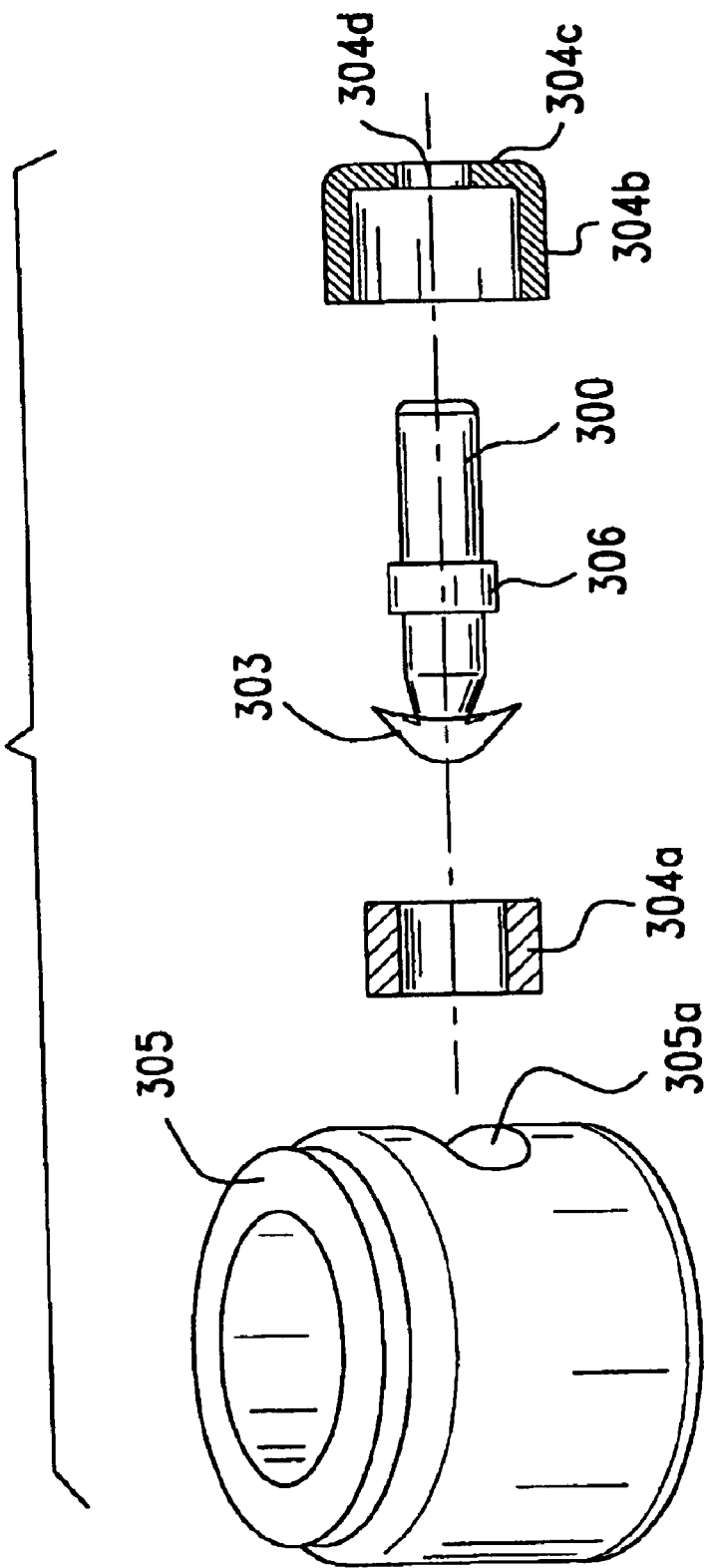

Mount 304 will now be described in more detail. Mount 304 preferably is manufactured as a first inner cylindrical tube 304*a* and an outer cylindrical tube 304*b*. Tube 304*a* has an inner diameter which is equal to the diameter of holes 301 and 305*a*. Tube 304*b* has an inner diameter which is equal to the outer diameter of tube 304*a*, and an inwardly projecting flange 304*c* at one end. Flange 304*c* defines a hole 304*d* having a diameter which is large enough to allow the outer end of peg 300 to reversibly slide therethrough, but which is small enough to prevent stop 306 from passing therethrough. An exploded view of this construction is shown in FIG. 9*f*. Tubes 304*a* and 304*b* are preferably ultrasonically welded to ring 305. If a simplified construction is desired, tube 304*a* may be omitted and the inner diameter of tube 304*b* may be set to be equal to the diameter of holes 301 and 305*a*. This allows mount 304 to be constructed from a single piece.

If desired, projection 303 may take the form of a frusto-conical tube made of a flexible material (FIG. 9*e*). The narrow end of the frusto-conical tube is rigidly fixed to the inwardly directed end of peg 300. The frusto-conical tube is coaxial with peg 300, and surrounds the inwardly directed end of peg 300, with the proviso that the overall length of the frusto-conical tube is less than the distance between the inwardly directed end of peg 300 and stop 306. When peg 300 is simultaneously pushed through holes 305*a*, 301, and 302, the sides of the frusto-conical tube collapse against the side of peg 300. After the peg and the frusto-conical tube attached thereto are pushed through hole 302, the sides of the frusto-conical tube expand. Since the large end of the frusto-conical tube has a diameter that is greater than the diameter of hole 302, peg 300 may not be withdrawn through the hole in the tubular sleeve.

In an alternative embodiment, projections or tube 303 may be rigid and non-flexible. If 303 is non-flexible, hole 302 should have a smaller diameter than the maximum diameter of tube 303 or the maximum distance across projections 303. After the projections or tube 303 penetrate hole 302, the upper ends of projections or tube 303 act as stops to prevent the peg 300 from being withdrawn through the hole in the tubular sleeve.

Figure 10A:
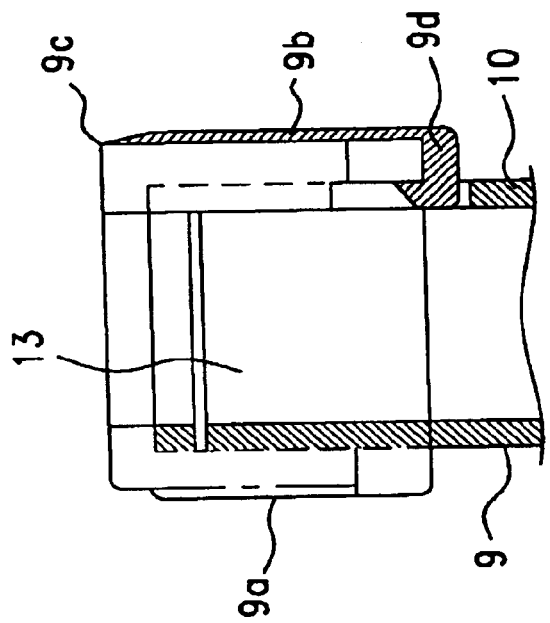
Figure 10B:
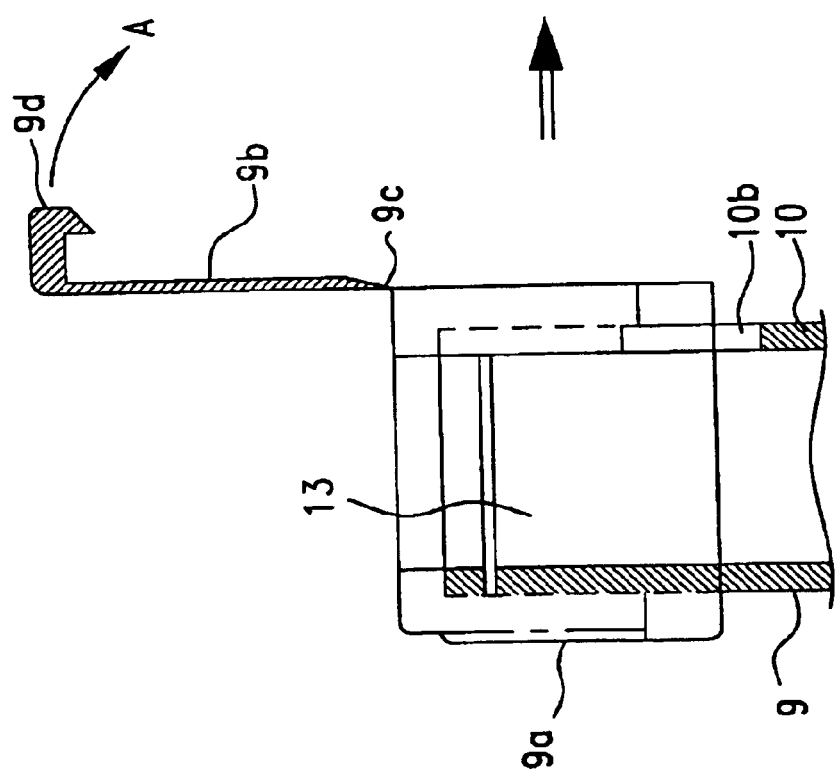

A third version of the mechanism for irreversibly engaging the pin at the second defined location in said longitudinal slot so as to hold said needle assembly in a position where the needle is retracted within the container is provided. This version of the mechanism features the rigid ring 9a mounted on wall 9 of the container; and a rigid tongue 9b attached to one end of the rigid ring by a living hinge 9c (FIG. 10a). This tongue is positioned so that it extends from the end of the container with syringe barrel-receiving opening 13. The second end of the rigid ring is substantially flush with one side of the slot 10b, without blocking slot 10b (slot 10c is not present in this embodiment). To permanently lock the needle assembly in a retracted position, pin 7 is moved into slot 10b, exactly as for the procedure for reversibly locking pin 7 into position. The rigid tongue is folded in the direction of arrow A against the external surface of the ring and irreversibly secured against the external surface of the ring so that the end of the rigid tongue blocks the opening of slot 10b while pin 7 is inside slot 10b. To accomplish this, the tongue is preferably designed so that it is collinear with slot 10 when it is in its initial, unfolded state, and has a length which is at least equal to the sum of the longitudinal length of the rigid ring and the width of slot 10b. To secure the tongue against the external surface of the ring, a hook 9d on the rigid tongue irreversibly snaps around the second end of the rigid ring (FIG. 10b). Hook 9d also blocks the opening to slot 10b. Alternatively, a post 9e on the rigid tongue may irreversibly snap into a hole 9f in the external surface of the rigid ring (FIG. 10c). A projection on the end of the rigid tongue fits into slot 10, blocking the opening to slot 10b (FIG. 10d).

One difficulty in manufacturing an article of this type lies in the difficulty in getting the pin on the needle assembly to properly engage slot 10. For example, the invention of D'Amico (vide supra) presents a substantially cylindrical hub having a radially protruding pin attached thereto positioned within a tubular container. The inner circumference of the container is substantially the same as the outer circumference of the hub. The pin is positioned within a slot in the wall of the container, where each end of the slot is closed. However, this article is difficult to manufacture inexpensively. When the hub slides into the container, the radially protruding pin is blocked by the end of the tubular container wall, and cannot readily enter the container.

This invention attempts to solve this problem. When the container is manufactured in one piece with a slot 10 which is closed at both ends, the combination of pin 7 and crosspiece 8 will not pass through slot 10 when the needle assembly of FIG. 1a is positioned inside the container of FIG. 2. To overcome this difficulty, one can position the needle assembly inside the container prior to attaching pin 7, and then insert pin 7 through slot 10 and secure the pin to sleeve 3. Alternatively, the container may be manufactured in two pieces, a tubular container and rigid ring 9a.

Figure 11:
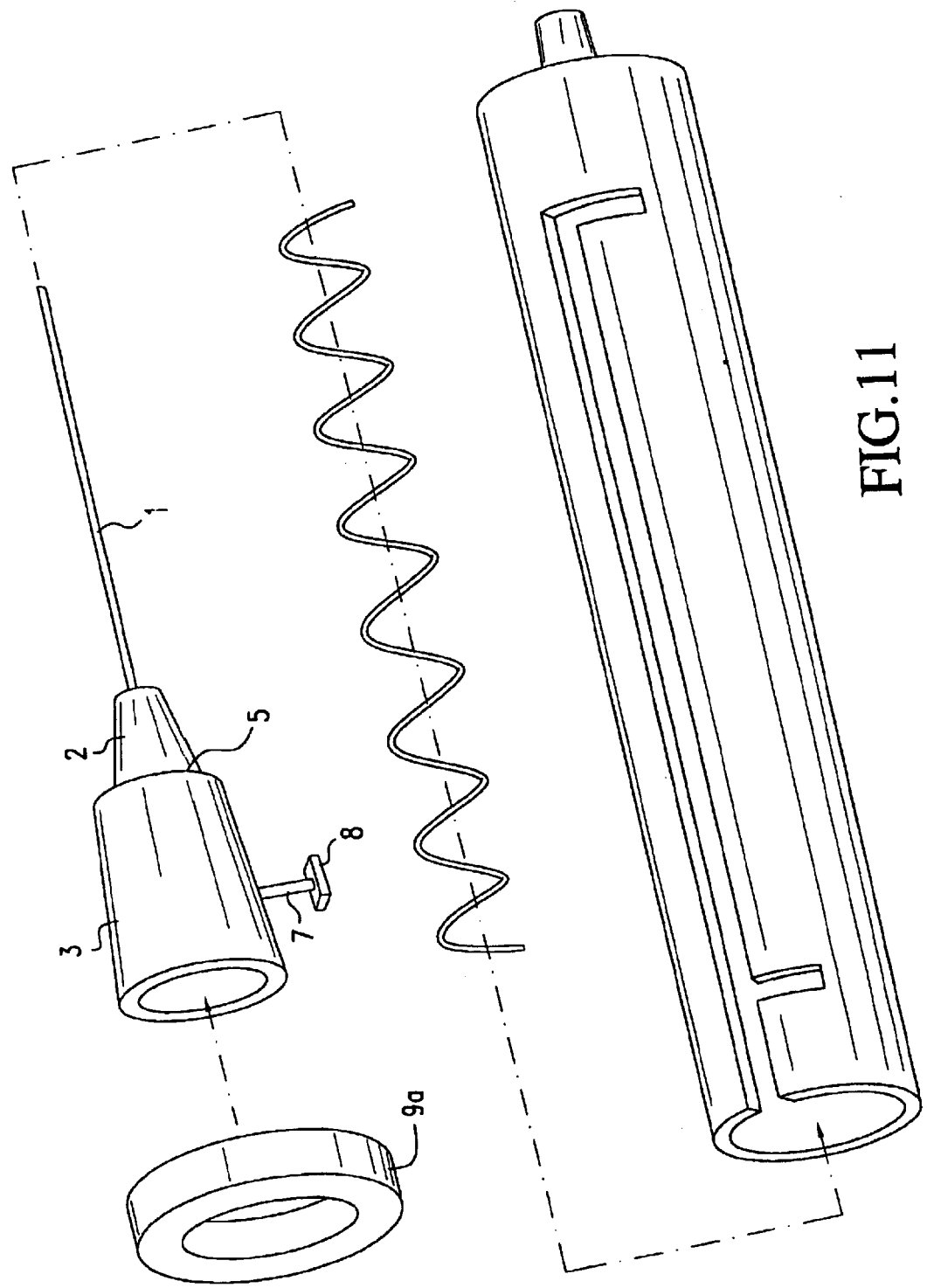
FIG. 11 is an exploded view of the syringe of the current invention, showing how the pieces are assembled.

The retractable syringe needle of the current invention maybe made by obtaining a needle assembly as previously described, and obtaining the previously-described container having a tubular wall 9 with an open-ended longitudinal slot 10 therein (FIG. 11). A spring or other biasing means is then inserted into the container. The needle assembly is then inserted into the syringe barrel-receiving end of the container so that pin 7 enters the open end of slot 10, and is slidably engaged by the longitudinal slot. The biasing means engages the hub of the needle assembly and reversibly biases the needle assembly toward a first position where the needle is concealed within the container. The rigid ring is then mounted on the container so that the ring closes the open end of slot 10, preventing the pin 7 from exiting slot 10.

Figure 12:
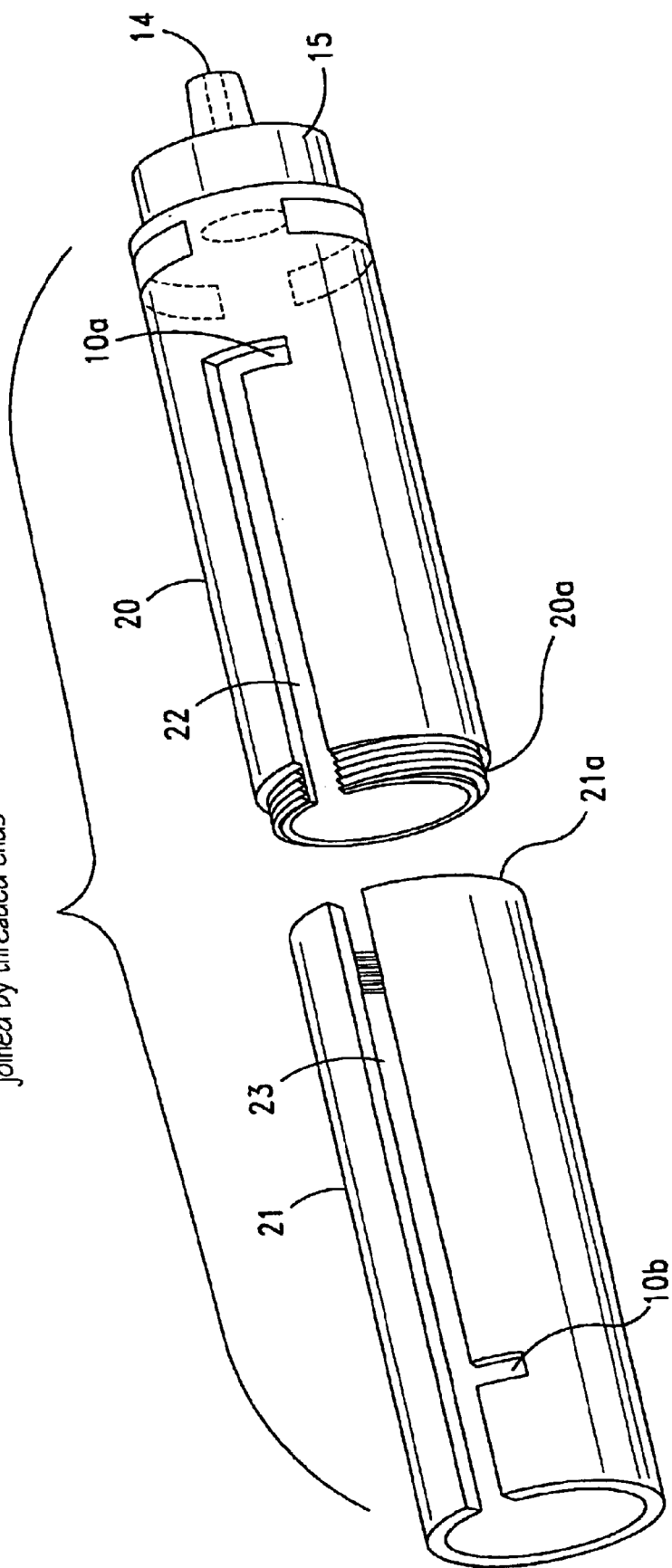
FIG. 12 illustrates the parts used to form an alternate version of the container of FIG. 2.

A second, and less preferred, method of solving the problem involves formation of the container in two parts, as shown in FIG. 12. The container is formed from an anterior portion 20 and a posterior portion 21. Anterior portion 20 has a first open end adapted to receive a syringe barrel and a second open end adapted to receive a hypodermic needle. Ridge 15 is positioned on the interior surface of the wall of anterior container portion 20. A first longitudinal slot 22 runs from the first end of the anterior portion of the container to point 12, near the second end of the anterior portion of the container. Slot 10a meets slot 22 at a right angle. Posterior portion 21 of the container has a first open end adapted to receive a syringe barrel and a second open end adapted to receive a syringe barrel. A second longitudinal slot 23 runs from the first end of the posterior portion of the container to point 11, near the second end of the posterior portion of the container. The first end of 20 and the first end of 21 are adapted to be joined together to form the complete container, by attaching 20 and 21 together so that slots 22 and 23 cooperate to form slot 10.

The manner in which 20 and 21 are joined together is not particularly limited. Parts 20 and 21 may be bonded together by means of a biocompatible adhesive, Alternatively, threaded ends on 20 and 21 maybe screwed together, and then secured with a suitable adhesive. Also, a ridge on an interior surface of one piece may snap into a groove on an exterior surface of another piece. The ridge may be treated with an adhesive prior to snapping it into the groove. Finally, if 20 and 21 are made from a thermoplastic material (i.e., polyolefin), they may be heat-sealed together. In the embodiment illustrated in FIG. 12, a threaded end 20a on container portion 20 is screwed onto a threaded end 21a on container portion 21.

The complete assembly is manufactured in the following manner, shown in FIG. 13. A spring 16 and the needle assembly are joined together by joining a first end of the spring to ridge 5 on hub 2. The needle 1 is positioned along the helical axis of the spring. This assembly is then positioned within the anterior portion 20 of the container so that a second end of the spring engages ridge 15. Container portion 20 is then joined to container portion 21 so that:

a) slots 22 and 23 line up to form slot 10; and b) pin 7 is slidably engaged by slot 10.

Alternatively, hub 2 may be positioned within posterior portion 21 so that pin 7 engages slot 23, and then part 20 may be joined to part 21 of the container so that the second end of the spring engages ridge 15. Again, when joining pieces 20 and 21, care should be taken to ensure that slots 22 and 23 are aligned so as to form a single slot 10 which engages pin 7.

This assembly method allows the safety needle to be assembled quickly and easily, and avoids the difficulty of trying to position the needle inside a fully assembled container without damaging the pin by forcing it past the rim of the container.

FIGS. 14 and 15 illustrate use of a syringe assembly with the safety needle of FIG. 3. The syringe comprises a syringe barrel 17, and a syringe plunger 18 slidably mounted therein. Barrel 17 has a frusto-conical tip 19 adapted to enter cavity 6 of sleeve 19 (cavity 6 is not shown in FIGS. 5 and 6, as it is occupied by tip 19.). Tip 19, after insertion into cavity 6, frictionally engages the interior of sleeve 3, forming a leakproof seal. A hole in tip 19 receives fluids which have passed through the bore of needle 1.

As shown in FIG. 15, syringe barrel 17 may be used to push the needle assembly within the container toward the second end of the container, compressing the spring and causing needle 1 to emerge through hole 14. In this position, the container encases at least a portion of barrel 17. Barrel 17 may then be rotated, causing sleeve 3 to rotate. This causes pin 7 to enter slot 10a, locking the syringe needle into position. The assembled syringe, with the needle exposed, may then be used to take a sample of a fluid. More particularly, the assembled syringe may be used to administer an injection to a patient, or to take a sample of arterial or venous blood from a patient.

After use, the contaminated needle may be discarded by rotating barrel 17 in the reverse direction to free pin 7 from slot 10a. This allows spring 16 to decompress, causing the container to slide forward off of the syringe barrel and cover needle 1. The syringe barrel may then be separated from sleeve 3, and the container with the needle concealed therein may be discarded with minimal risk of injury from contact with the contaminated needle. The syringe barrel and plunger may be discarded, or sterilized in an autoclave for reuse.

As shown in FIG. 16, it is possible to secure two pins 7, each having a crosspiece 8 mounted thereto, on a single needle assembly, where the two pins are directed in opposite directions. Such a needle assembly may be mounted in a container having two slots 10a in opposite sides of wall 9. A transverse slot 10a intersects each slot 10, with each slot 10a running in the same direction (i.e., either clockwise or counterclockwise, when viewed from the second end of the container along the container axis). This version of the apparatus operates in the same manner as the assembled apparatus of FIG. 3. The only difference is that the presence of the second pin anchors hub 2 of the needle assembly more firmly along the axis of the container (FIG. 17).

Figure 18:
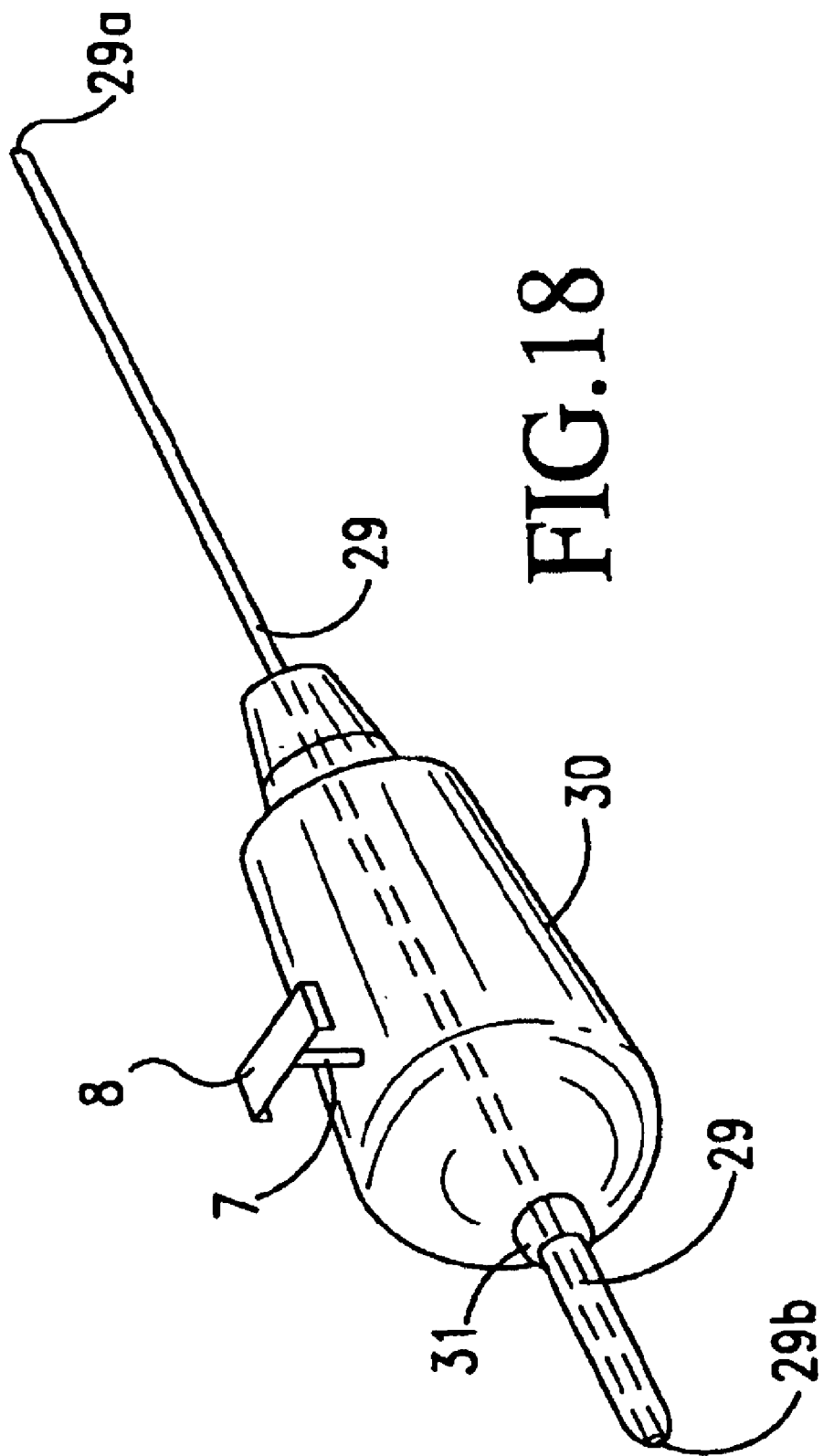
FIG. 18 shows a modified version of the needle assembly of FIG. 1a, for use in taking blood samples.

FIG. 18 shows an alternative embodiment of the needle assembly of FIG. 1a. This embodiment of the needle assembly features a hollow straight needle 29 having two ends. The needle 29 extends through a hub 30, so that a first end of the needle 29a points in a forward direction, and a second end of the needle 29b points in a reverse direction. Pin 7 is rigidly connected with said hub, and extends in a radial direction. Crosspiece 8 is connected with the pin at a defined distance from the hub. Preferably, a rubber sheath 31 covers end 29b of needle 1.

Figure 19:
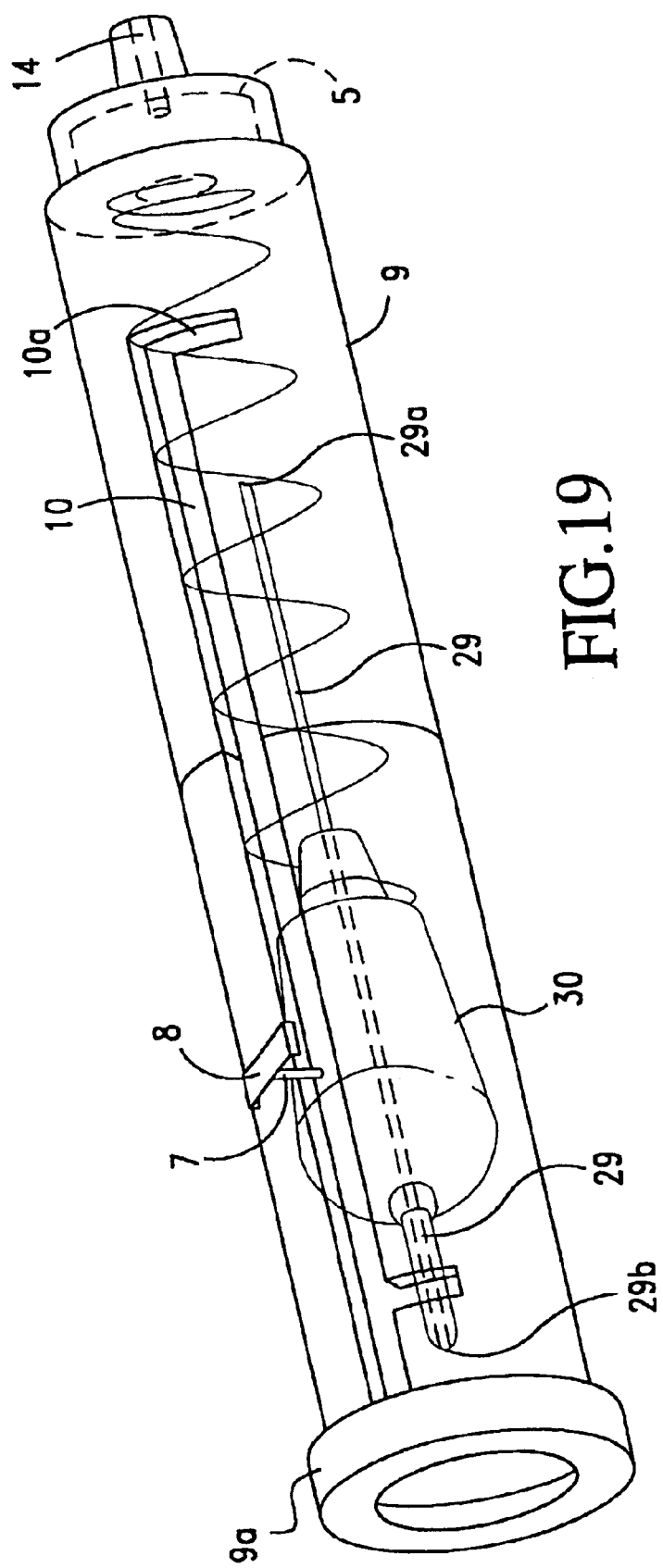
FIG. 19 shows an apparatus for taking blood samples, using the needle assembly of FIG. 18.

FIG. 19 shows the needle assembly of FIG. 18 mounted within a container similar to that of FIG. 2. The container features a defined cylindrical axis and has a tubular wall 9 with a longitudinal slot 10 therein. A first open end of the container is adapted to receive a receptacle for venous blood, preferably an evacuated test tube with a rubber stoppers and a second open end adapted to allow the first end of the hollow needle to pass therethrough. The longitudinal slot extends from the first open end of the container to a defined point near the second open end of the container, where the longitudinal slot is open-ended at the first open end of the container and closed at the second open end of the container. A rigid ring is positioned over the first open end of the container so as to close the open end of the longitudinal slot. A plurality of circumferential strengthening ridges may be positioned on the exterior surface of the container. The needle assembly is mounted within the container so that (i) the first end of the needle, 29a, is directed toward the second open end of the container, and (ii) pin 7 on the needle assembly is slidably engaged by longitudinal slot 10, with crosspiece 8 acting to support hub 30 so that it is positioned on the axis of the container. End 29a of needle 29 is exposed by using the thumb or finger to manually slide piece 8 forward toward needle-receiving opening 14, carrying hub 30 toward the second end of the container until the needle end 29a passes through opening 14 and is exposed. Piece 8 is then pushed sideways until pin 7 enters slot 10a, locking the needle into the exposed position. The needle may then be inserted into a patient's blood vessel. The rubber sheath prevents the patient's blood from traveling through the needle. Positioned inside the container, there is a spring or other means for biasing the needle assembly towards a position where the needle is concealed inside the container; the biasing means acts to prevent premature exposure of the needle.

The double-ended safety needle additionally features a first notch 10a which intersects the longitudinal slot at a first defined location near the needle-receiving opening 14 in the container. The needle may be reversibly secured in an exposed position by pushing pin 7 toward opening 14 until pin 7 is positioned adjacent to notch 10a, and then pushing pin 10b sideways into notch 10a. The biasing means presses the pin against the rear wall of notch 10a, securing the needle assembly into position. Similarly, the needle may be reversibly secured in a concealed position by pushing pin 7 toward opening 13 until pin 7 is positioned adjacent to a second notch 10b near opening 13 in the container, and then pushing pin 10b sideways into notch 10b. As previously described, each of notches 10a and 10b may be straight transverse notches, or notches 10a and 10b may each independently be a T-shaped notch (as seen in FIG. 6a), a L-shaped notch (FIG. 6b), or a C-shaped notch (FIG. 6c). Also, each notch may be provided with teeth 200 which are spaced sufficiently closely together that the pin may not be pushed into, or out of, the notch without the deliberate application of force.

Figure 8A:
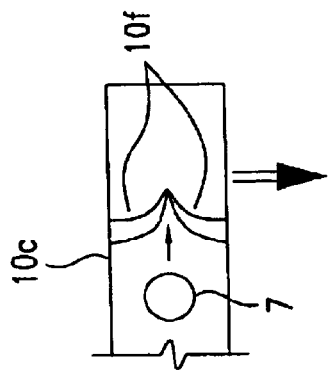
Figure 8B:
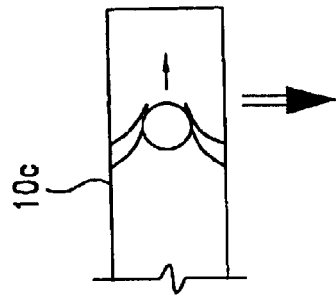
Figure 8C:
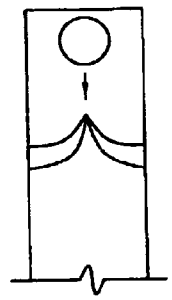

A means for irreversibly engaging the needle assembly in a retracted position comprises a third notch 10c, where notches 10b and 10c are collinear and extend in opposite directions from the longitudinal slot as seen in FIGS. 7 and 8. A pair of flexible projections having tips which contact each other extend from opposite sides of notch 10c. The tips are adapted to allow the pin engaged by the slot to pass therethrough when the pin enters notch 10c from the longitudinal slot, and to not allow the pin to pass therethrough to exit notch 10c.

Alternatively, the means for irreversibly engaging the pin may comprise a radially projecting peg 300 which is secured to the rigid ring by a tubular mount 304, substantially as seen in FIGS. 9a and 9b. The tubular mount preferably takes the form of a cylinder having a defined axis, where the defined axis of the cylinder is directed radially outward from the surface of the housing. The rigid ring is positioned so that one end of the rigid ring is substantially flush with one side of notch 10b (no notch 10c is present in this embodiment). To secure the pin in notch 10b, the peg is pushed through a series of coaxial holes 305a, 301, and 302, through the ring, the sheath 9, and the sleeve 3, respectively. Projections 303 on peg 300 then spread out and prevent peg 300 from being withdrawn through hole 302, effectively locking the needle assembly in place, relative to sleeve 9. The peg must be short enough that it will not interfere with the rearwardly projecting end of the hollow needle.

Additionally, the means for irreversibly engaging the pin may comprise a rigid tongue attached to one end of the rigid ring by a living hinge, as seen in FIGS. 10a through 10d. The rigid ring is positioned so that the other end of the rigid ring is substantially flush with one side of notch 10b (no notch 10c is present in this embodiment). To secure the pin in notch 10b, the rigid tongue is folded against an external surface of the ring and irreversibly secured against the external surface of the ring so that the end of the rigid tongue blocks the opening of the second notch.

To hold the rigid ring in position relative to the wall of the container, a circumferential ridge $9_g$ on the interior surface of the rigid ring 9a snaps into a circumferential groove 9h on the exterior surface of the container (FIG. 20). Also, a ridge 9i on the interior of the rigid ring may fit into the open end of slot 10 to prevent rotation of the ring relative to the slot.

Figure 21:
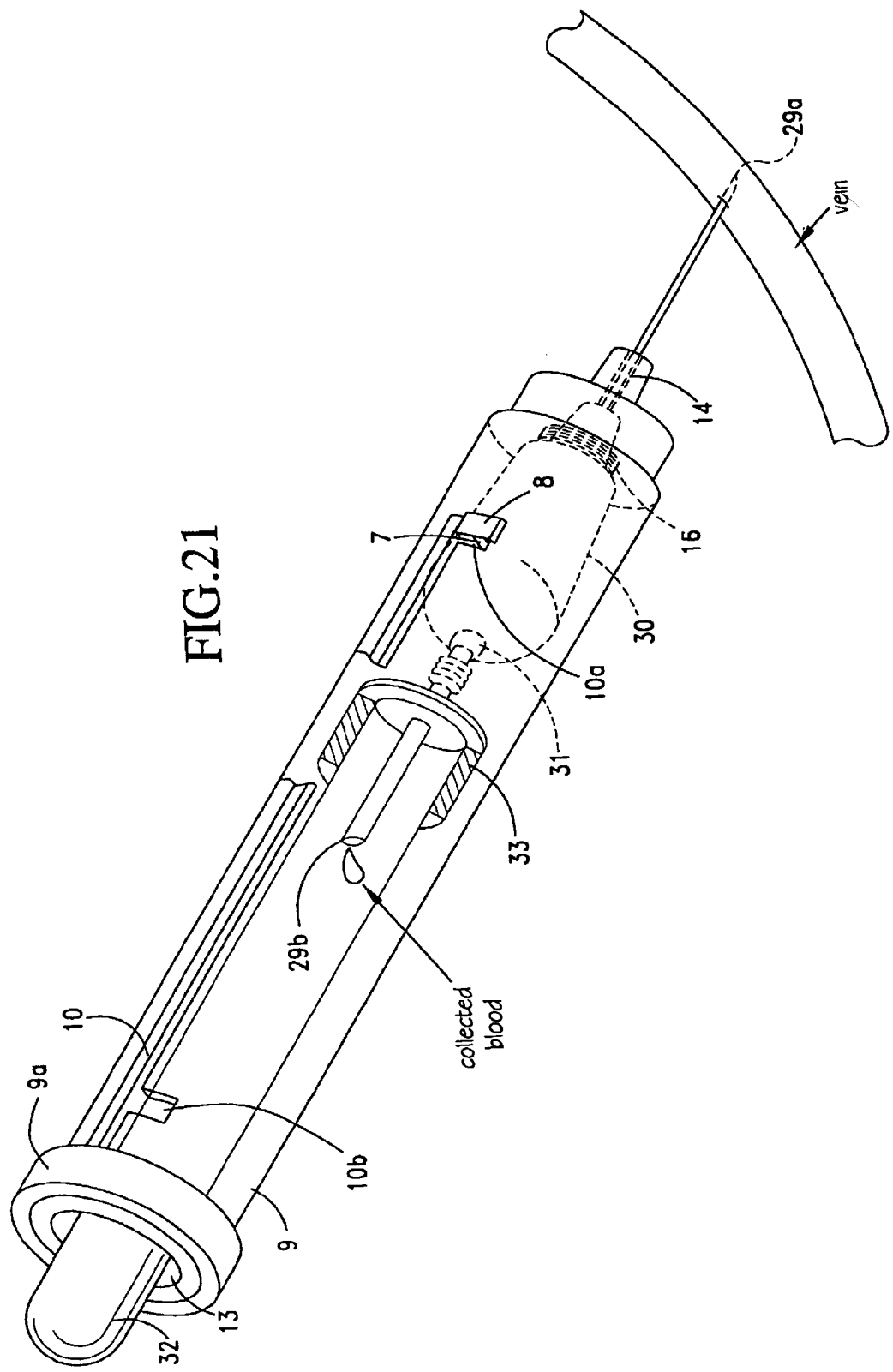
FIG. 21 shows the apparatus of FIG. 19 in use.

The assembly of FIG. 19 may be used with a receptacle for receiving a blood sample, as shown in FIG. 21. This receptacle is a test tube 32 having an open end. A rubber septum 33 seals the open end of the test tube. The interior of the test tube may be under vacuum. While needle 29 is in the patient's blood vessel, the end of the test tube which is sealed by septum 33 is inserted into opening 13 of the container until septum 33 contacts rubber sheath 31. The test tube is then pushed toward hub 30, and septum 33 pushes the end of rubber sheath 31 along needle 29 toward hub 30, exposing end 29b of needle 29. End 29b of needle 29 pierces the rubber sheath 31 and septum 33, entering the test tube. Blood from the patient then travels through hollow needle 29 into the test tube. After taking a sample of the patient's blood, test tube 32 is removed from the container. Rubber sheath 31 resumes its original configuration, covering end 29b of the needle and cutting off the flow of blood. Needle 29 is then withdrawn from the patient's blood vessel. Crosspiece 8 is then pushed sideways until pin 7 exits slot 10a, unlocking the needle. Spring 16 then causes needle 1 to withdraw into the container.

As in the syringe needle assembly of FIG. 3, piece 8 is sufficiently large that it cannot pass through slot 10 into the interior of the container, and is rigidly secured to a defined position along the length of pin 7, where the defmed position on pin 7 is chosen so that hub 30 of the needle assembly is positioned along the cylindrical axis of the container. More particularly, the distance between the axis of hypodermic needle 1 and crosspiece 8 is equal to the one half the external diameter of the wall 9 of the container. This retains needle 29 along the axis of the container.

The use of crosspiece 8 to retain needle 1 in position is particularly important in an apparatus for obtaining blood samples. The container has to be wide enough to receive the test tube, which in turn is normally wider than hub 2. Without crosspiece 8, pin 7 would slip out of slot 10, and end 29b of needle 29 would fall against the inner surface of wall 9. Needle 29b would then be incorrectly positioned to penetrate septum 33.

A threaded male joint 34 may surround opening 13 at the first end of the container of FIG. 2, and a threaded male joint 35 may surround opening 14 at the second end of the container. Cap 36 having a threaded female joint may be screwed onto joint 34, covering opening 13, and cap 37 having a threaded female joint may be screwed onto joint 35, covering opening 14. This is normally done whenever the needle is not intended to be exposed, so as to minimize the risk of accidental contact with the tip of the needle.

Figure 22:
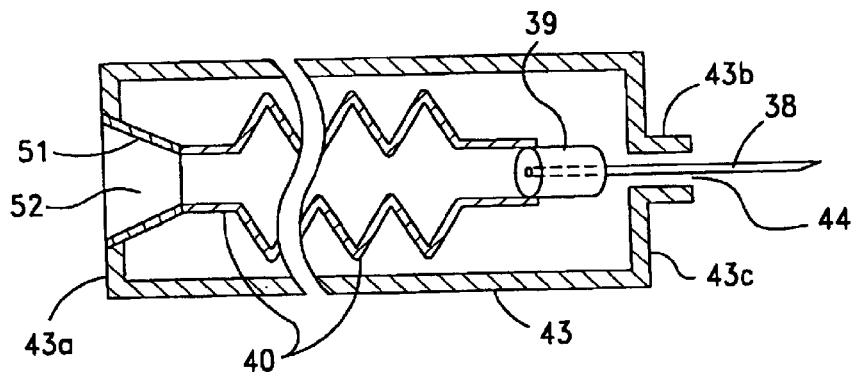

A further embodiment of the invention will now be discussed. This embodiment, shown in FIG. 22, features a hollow hypodermic needle 38 and a cylindrical hub 39 having an axial passage therethrough. The hollow needle is rigidly connected with the hub so that the axial passage and the interior of the hollow needle form a continuous conduit. Hub 39 is secured to one end of an adjustable-length tube 40 so that the interior of hollow needle 38 makes fluid contact with the interior of tube 40. The tip of a syringe barrel, which may be cylindrical or frusto-conical, may be frictionally secured to the other end of the adjustable-length tube so that the interior of the syringe barrel is in fluid communication with the interior of the adjustable-length tube. Tube 40 is preferably impermeable to liquids, non-elastic, and axially collapsible. By collapsing the tube in an axial direction, the length of tube 40 may be changed from a first extended length to a second contracted length. The tube may then be extended in an axial direction, restoring the length of the tube to the first extended length.

A tubular sheath 43 is disposed around the adjustable-length tube 40. The tubular sheath 43 has a first end 43a which is rigidly connected with the first end of the adjustable-length tube and a second end 43b having an opening 44 which is sufficiently large to allow the end of the hypodermic needle 38 to pass therethrough. The outer surface of member 51 is rigidly secured to end 43a of sheath 43. When the apparatus is not in use, the opening at each end of the tubular sheath may be covered by a cap (not shown in the drawings). The caps may screw onto the sheath, or snap onto the sheath.

The preferred means of connecting the adjustable-length tube 40 to sheath 43 is by means of a collar ring 40e which comprises an outer skirt 40f which fits over the outer surface of sheath 43 (FIG. 23c). The outer skirt is connected with an inner skirt 40g which fits inside sheath 43. A female joint 40h is rigidly connected with the inner skirt of collar ring 40e in such a way that a syringe barrel may be inserted into the inner skirt of collar ring 40e and engage joint 40h. The inner and outer skirts of collar ring 40e are connected by a rigid ring 40i.

Figure 22A:
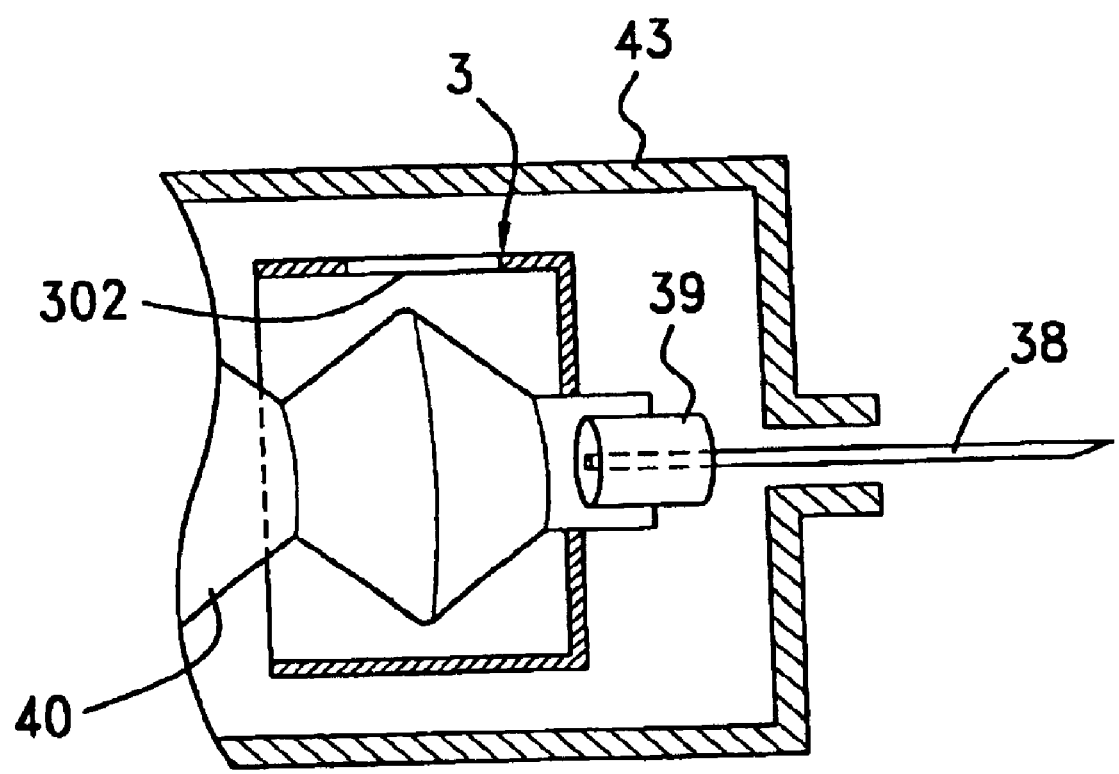

The retractable needle featuring the adjustable-length tube additionally features a means to alter the length of the adjustable-length tube from the contracted length to the extended length. This length-altering means includes a longitudinal slot running along the length of the tubular sheath; and a knob or pin 7 connected to the hub of the needle assembly. The knob or pin slidably engages the longitudinal slot, and may be used to change the length of the adjustable-length tube from its collapsed state to its extended state. The retractable needle additionally features a means for reversibly securing the knob at a first position along the length of the longitudinal slot, where the tube is contracted when the knob is in said first position; a means for reversibly securing the knob at a second position along the length of the longitudinal slot, where the tube is extended when the knob is in said first position; and a means for irreversibly securing the knob at said first position along the length of the longitudinal slot The structures of the reversible and irreversible securing means are substantially as previously described, with the following provisos. If the peg-based permanent locking mechanism of FIG. 9a is used, it is preferred that the sleeve 3 having hole 302 therethrough be coaxial with adjustable-length tube 40, with a gap which is sufficiently large to receive the end of peg 300 therebetween (FIG. 22a). That allows the peg 300 to penetrate hole 302, engaging sleeve 3, without allowing fluid flowing through the adjustable-length tube to escape through hole 302.

Figure 23A:
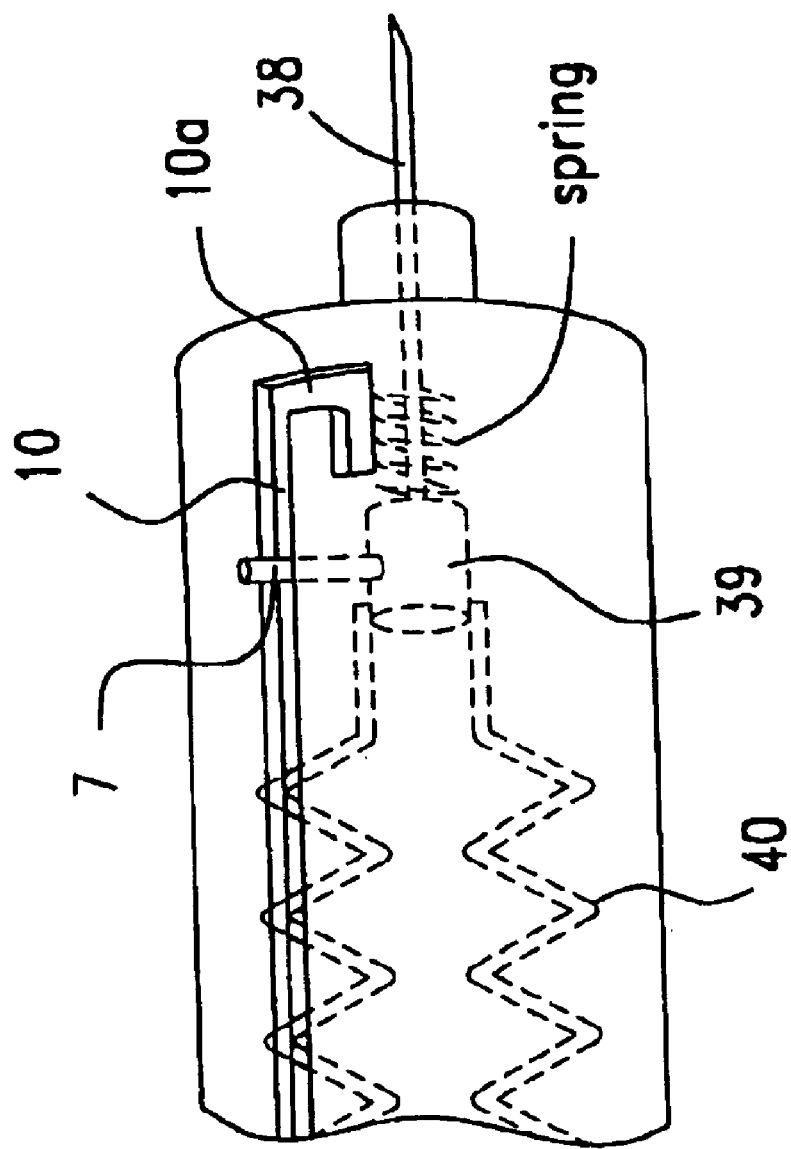

Also, one preferred mechanism for locking the needle in the exposed position for an embodiment using an adjustable length tube involves the use of an L-shaped slot 10a (FIG. 23a). The adjustable-length tube is extended, and radially projecting member 7 connected to hub 39 is pushed sideways into a transverse branch of slot 10*a*, and then backwards into the longitudinal branch of slot 10*a*. Although not necessary, a short spring may be attached to the hub or to the interior of the sheath 43, near end 43*b* having the opening for the needle. The spring acts to bias the hub, and radially projecting member 7 attached thereto, backwards, so that member 7 is pressed against the rear wall of the longitudinal branch of slot 10*a*. This holds the hub in position until the user is ready to retract the needle.

Figure 23B:
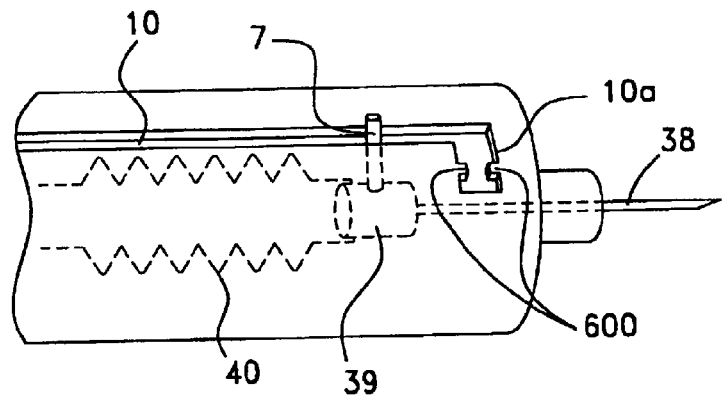

Alternatively, another preferred mechanism for locking the needle in the exposed position for an embodiment using an adjustable length tube involves the use of a slot 10*a* having teeth 600 (FIG. 23*b*). The gap between teeth 600 is less than the width of the radially projecting member 7, but is large enough the member 7 can be pushed between teeth 600. The adjustable-length tube is extended, and radially projecting member 7 is pushed sideways into slot 10*a* through teeth 600. The teeth act to prevent member 7 from accidentally leaving slot 10*a*, holding the hub in position. Member 7 can be pushed out of slot 10*a* through teeth 600 when the user is ready to retract the needle. No spring is required in this embodiment.

Figure 24A:
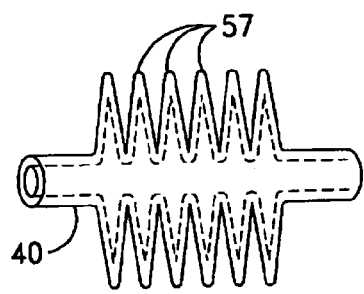
FIGS. 24a, 24b, 25a, and 25b show different embodiments of the adjustable-length tube.
Figure 24B:
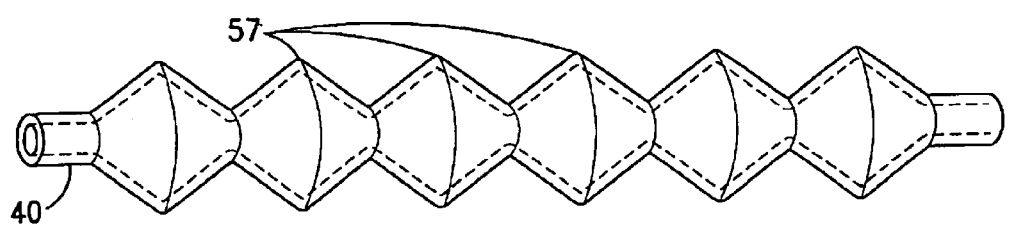

The preferred embodiments of the adjustable-length tube 40 will now be discussed. The most preferred type of adjustable-length tube 40 contemplated for use in this invention features a series of circumferential pleats 57 disposed along the length of the tube, as shown in FIGS. 23*a* and 23*b*. When tube 40 is in its contracted or collapsed state (FIG. 24*a*), pleats 57 are folded together. The adjustable-length tube may be lengthened by pulling one end of tube 40 (the end to which the hub is attached) away from the other, causing pleats 57 to unfold (FIG. 24*b*).

Figure 25A:
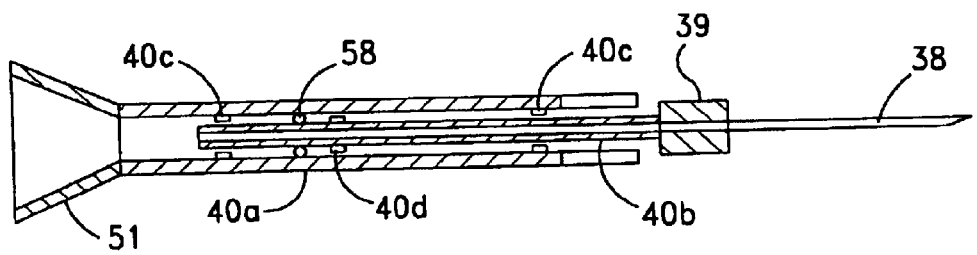
Figure 25B:
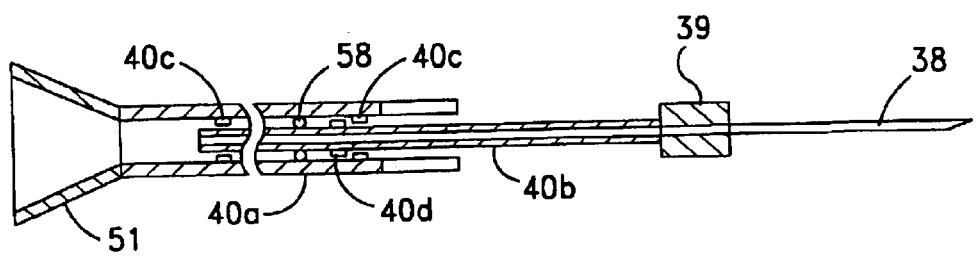

Another embodiment of adjustable-length tube 40 is a telescoping tube made from an outer tube 40*a* and an inner tube 40*b*, as shown in FIGS. 25*a* and 25*b*. The inner tube is slidably disposed within the outer tube. A first end of outer tube 40*a* is adapted to be secured to syringe barrel 40 through conical member 51, as previously described. A first end of inner tube 40*b* is adapted to be secured to hub 39. The inner tube 40*b* may be moved from a position where tube 40*b* is entirely or primarily disposed within tube 40*a* (FIG. 25*a*), contracting tube 40, to a position where tube 40*b* is mostly exposed (FIG. 25*b*), expanding tube 40. Ridges 40*c* on the interior of outer tube 40*a* interact with a ridge 40*d* on the outer surface of tube 40*b*, acting as stops to prevent removal of tube 40*b* from tube 40*a*. Preferably, a leakproof sealing material 58 is disposed between the outer surface of the inner tube and the inner surface of the outer tube. This sealing material may be a hydrophobic, biocompatible polymer with a low coefficient of friction, such as silicone or teflon.

Figure 25C:
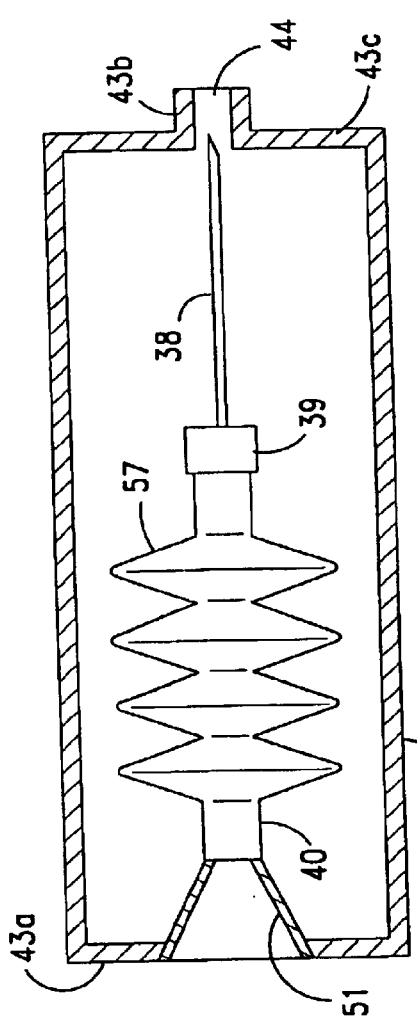
Figure 25D:
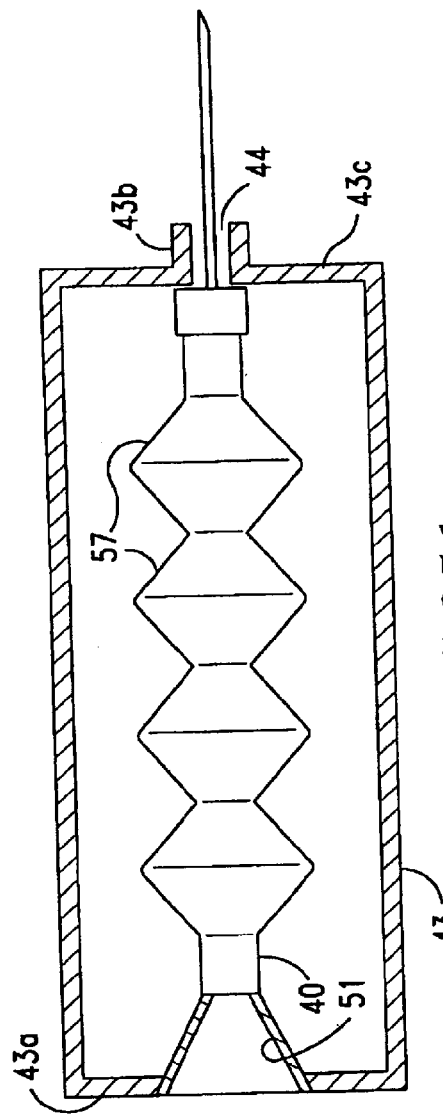

When the adjustable-length tube is contracted, the hypodermic needle is entirely disposed within the sheath (FIG. 25*c*). When the adjustable-length tube is extended, the end of the hypodermic needle is exposed through opening 44 in the second end of the sheath (FIG. 25*d*). If desired, the interior diameter of the sheath 43 may narrow from a diameter which is great enough to receive the adjustable-length tube 40 to a diameter which is little greater than the diameter of needle 1. This narrowing occurs at a point 43*c* near the opening 44. When the needle is disposed within the sheath, the pointed end of the needle then occupies a position where the inner diameter of the container is small (FIG. 19*a*). This helps prevent the needle point from moving away from the axis of the container. If desired, a spring or other biasing means may bias the hub away from opening 44. This causes the adjustable-length tube to preferentially occupy its contracted state, with the needle being retracted within the container.

Preferably, the adjustable-length tube is connected to the syringe barrel by means of an adaptor 500. The adaptor fits inside the end of sheath 43, and is rigidly connected to the adjustable-length tube. The adaptor further includes a cavity 501 adapted to frictionally engage the end of a syringe barrel. This cavity is in fluid communication with the interior of the adjustable-length tube. A collar ring 502 is secured to the end of adaptor 500 in such a way that a gap 503 is defined between an exterior surface of the adaptor and an interior surface of the ring 502. The end of sheath 43 then slides into this space 503, and is rigidly secured to the exterior surface of the adaptor and/or to the interior surface of the ring 502.

Figure 26:
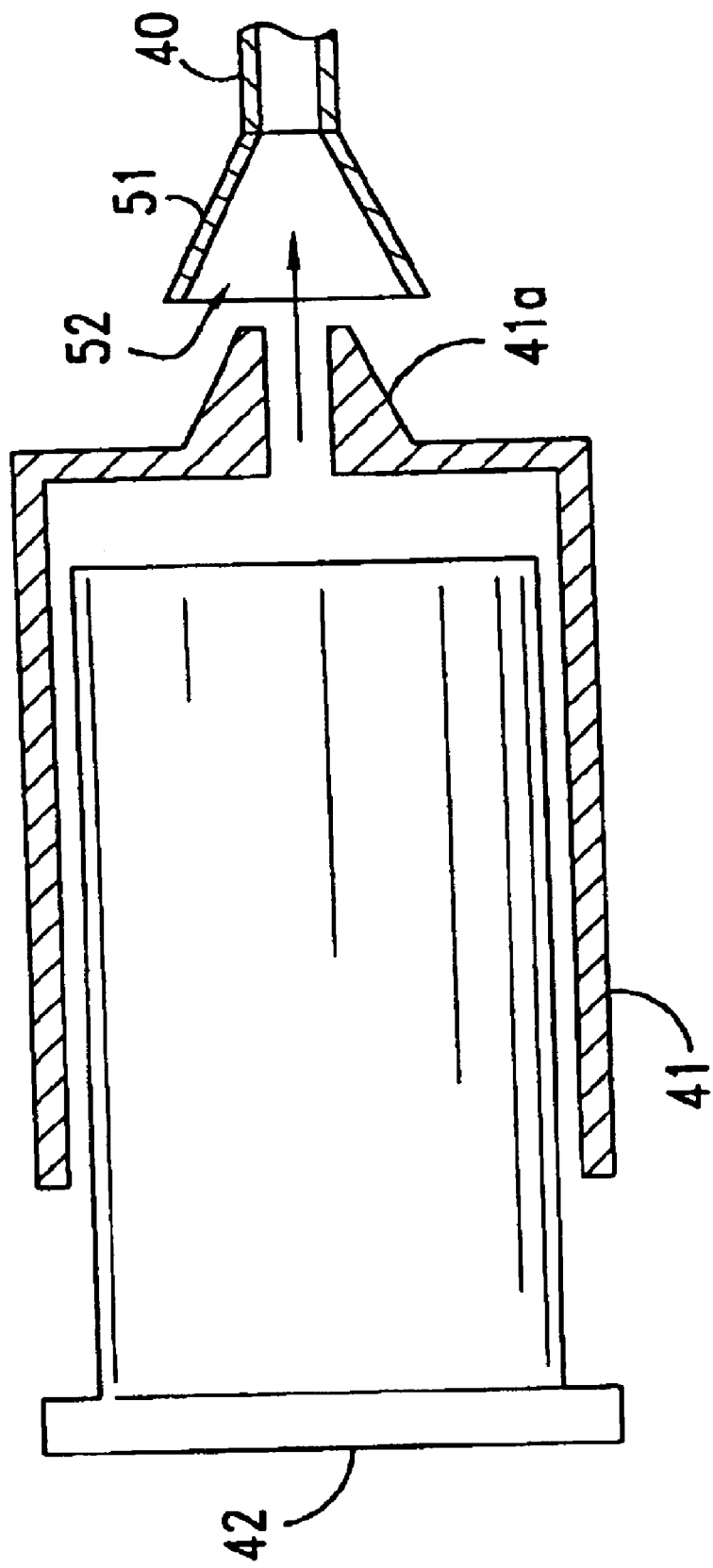
FIG. 26 shows the apparatus of FIG. 22 in use.

This embodiment of the invention may be used to withdraw fluid samples from a patient's bloodstream, or to inject medicinal fluids into a patient's bloodstream. A syringe barrel 41 having a plunger 42 slidably mounted therein may be reversibly secured to the other end of the adjustable-length tube 40 so that the interior of the syringe barrel is in fluid contact with the interior of the adjustable-length tube, as shown in FIG. 26. By raising the plunger and creating a partial vacuum within barrel 41, fluids may then be drawn through needle 38 (not shown in FIG. 26) and tube 40 into barrel 41. The syringe barrel 41 is secured to the first end of the adjustable-length tube 40 by means of a hollow conical member 51. The inner surface of member 51 defines a cylindrical or frusto-conical cavity 52 adapted to frictionally engage the tip 41*a* of the syringe barrel. The conical member 51 has a passage 51*a* therethrough. Member 51 is connected to the end of the adjustable-length tube 40 to which hub 39 is not secured. The cavity 52 makes fluid contact with the interior of the adjustable-length tube 40 through the passage 51*a*. As the outer surface of member 51 is rigidly secured to the first end of the tubular sheath 43 (sheath 43 is not shown in FIG. 21), sheath 43 is immobile relative to a syringe barrel 41 connected to tube 40.

Figure 27:
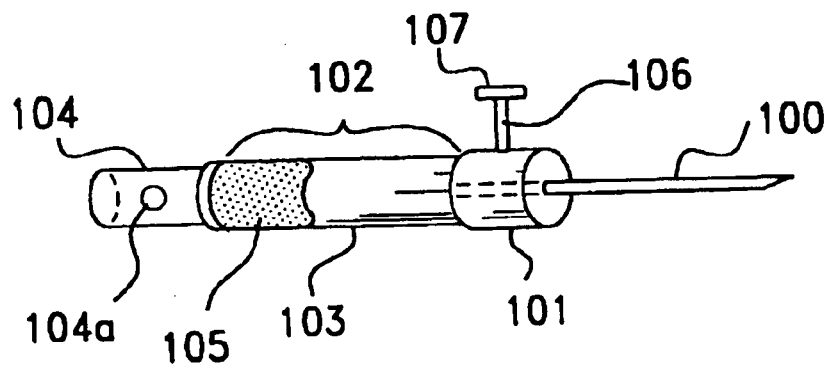
FIG. 27 shows a needle assembly for use with a catheter.
Figure 28:
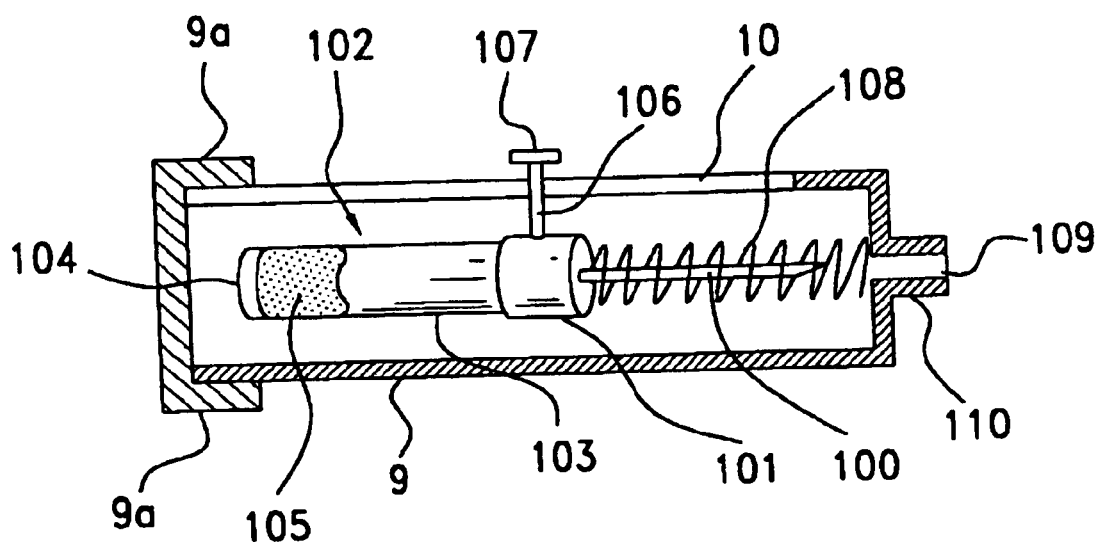
FIG. 28 shows a retractable needle for use with a catheter.
Figure 30:
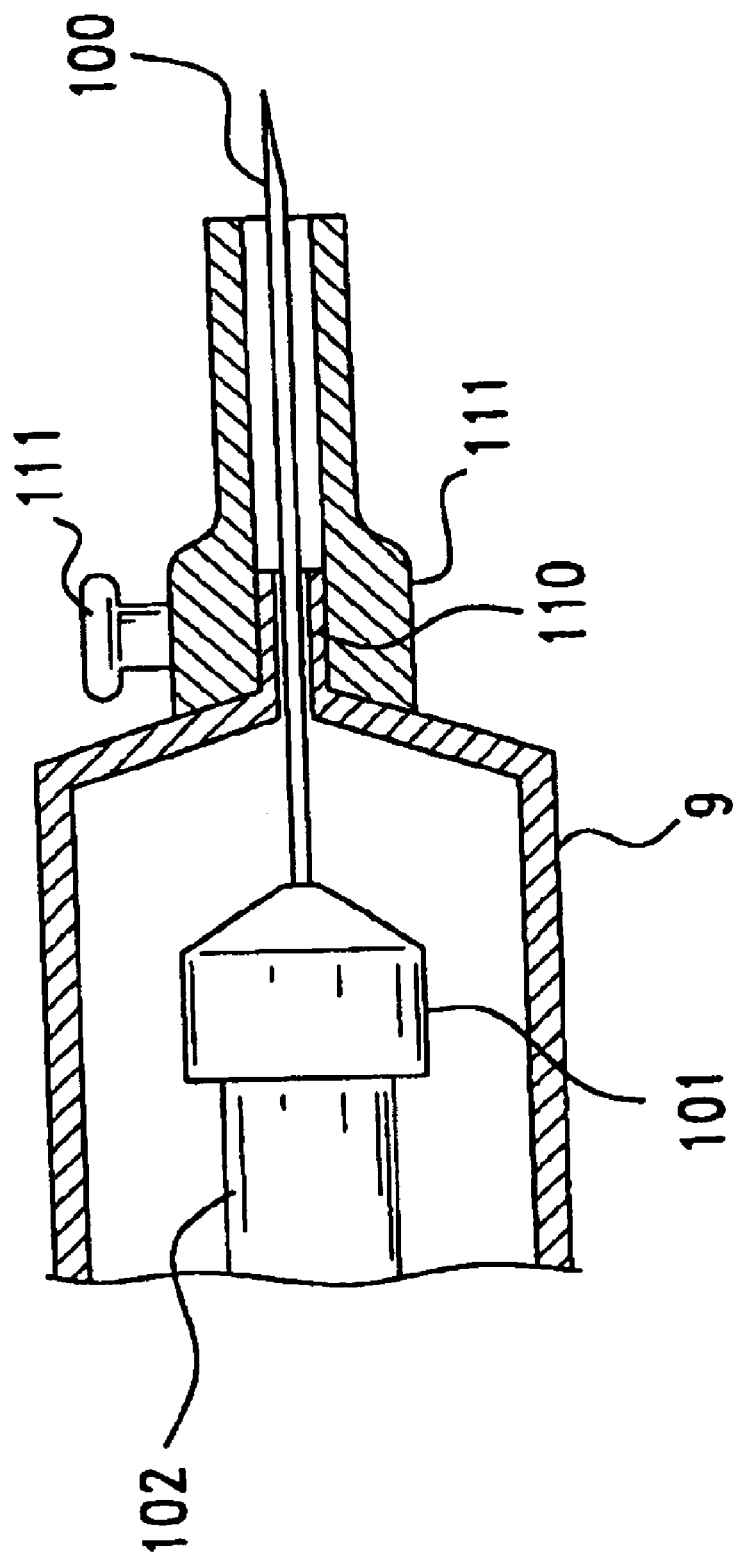
FIG. 30 shows the needle assembly of FIG. 28 with a catheter attached thereto.

A needle assembly for use with a catheter is assembled as shown in FIG. 27. Hollow needle 100 extends from one end of a cylindrical hub 101, and penetrates the second end of the hub. The second end of the hub is connected to a flash chamber 102 which features a tubular side wall 103 having a first end which makes a watertight seal with the second end of hub 101. A small plug of absorbent material 105, such as cotton, is normally present in flash chamber 102, and closes the second end of tubular wall 103, preventing leakage of fluids from the flash chamber. The interior of flash chamber 102 is in fluid communication with the interior of hollow needle 100, so that fluid may travel through the needle 100 into chamber 102. The tubular wall of chamber 102 is normally transparent or translucent, so that blood entering the flash chamber through needle 100 is readily visible. A stem 106 protrudes radially from hub 101. A thumbrest 107 is attached to stem 106. A sleeve 104 may project from the end of the flash chamber opposite to needle 100; this sleeve may have a radially directed hole 104*a* therethrough. The needle assembly having the flash chamber is positioned inside a container with a defined cylindrical axis having a tubular wall 9 with a longitudinal slot 10 therein. The container has a first end having an opening 109 adapted to allow the hollow needle to pass therethrough and a closed second end. A tubular extension 110 of the container surrounds opening 109. Additionally, a pair of finger rests 400 is positioned on opposite sides of the container, with slot 10 running therebetween (FIG. 30). The finger rests 400 are useful for gripping wall 9 of the container when inserting the needle into a patient. The pin of the needle assembly is slidably engaged by the longitudinal slot in the container, so that said needle assembly may be moved from a first position where the needle is within the container to a second position where the needle is exposed by sliding the pin toward the first end of the container. A spring 108 reversibly biases the needle into the first position. A notch 10a may be used to reversibly retain the needle in an exposed position, while a notch 10b may be used to reversibly retain the needle in a retracted position, exactly as previously described. A means for irreversibly retaining the needle in its retracted position may comprises a third notch 10c, where notches 10b and 10c are collinear and extend in opposite directions from the longitudinal slot. A pair of flexible projections having tips which contact each other extend from opposite sides of the third notch, directed away from slot 10. The projections allow the pin engaged by slot 10 to pass therethrough when the pin enters notch 10c from the longitudinal slot, and to not allow the pin to pass therethrough to exit notch 10 (FIGS. 7 and 8). Alternatively, the container may comprises a housing having a first open end adapted to admit the needle assembly and a second open end adapted to admit the hollow needle, and a cap 9a at the first open end of the housing The longitudinal slot extends from the first open end of the housing to a defined point near the second open end of the container, said longitudinal slot being open-ended at the first open end of the container and closed at the second open end of the container. Cap 9a blocks the open end of the longitudinal slot. The cap has a skirt that extends over the exterior of the housing until it reaches the edge of the first notch. Cap 9a may also serve to close the opening at the first open end of the housing. However, this is not necessary; cap 9a may leave an opening allowing access to the interior of the housing.

Figure 29:
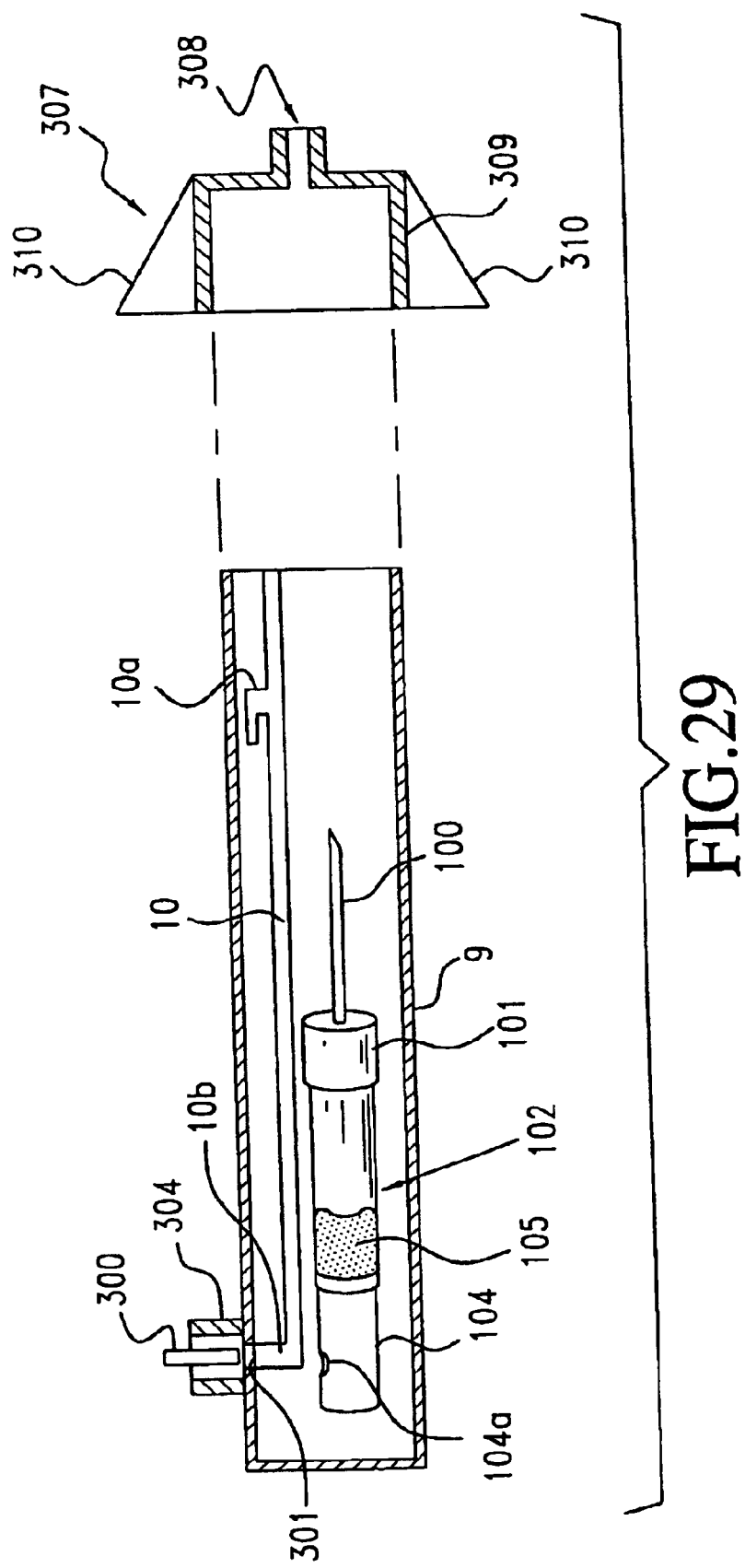
FIG. 29 shows a preferred housing design for use with a catheter.

The needle for use in catheter insertion further comprises a means for permanently locking the needle in a retracted position. For example, a rigid tongue may be attached to the cap by a living hinge. After pin 7 is positioned in slot 10b, the rigid tongue may be folded against the skirt of the cap and irreversibly securing against the external surface of the skirt so that the end of the rigid tongue blocks the opening of 10b, preventing pin 7 from exiting notch 10b, exactly as previously described (FIGS. 10a through 10d). Alternatively, the means for irreversibly engaging the pin may comprise a radially projecting peg 300 which is secured to the cap 9a by a tubular mount 304, substantially as seen in FIGS. 9a and 9b, where cap 9a takes the place of 305. To secure the pin in notch 10b, the peg is pushed through a series of coaxial holes 305a, 301, and 302, through the cap 9a, the sheath 9, and a sleeve secured to the flash chamber, respectively. The sleeve is secured to the opposite end of the flash chamber from the hub. Projections 303 on peg 300 then spread out and prevent peg 300 from being withdrawn through hole 302, effectively locking the needle assembly in place, relative to sleeve 9. Alternatively, the means for irreversibly engaging the pin may comprise a radially projecting peg 300 which is secured directly to sheath 9 by a tubular mount 304, with cap 9a being omitted. A bore through the tubular mount 304 is aligned with a hole 301 through the wall of sheath 9. Peg 300 may then be pushed through hole 301 in the sheath 9 and through hole 104a in the sleeve 104 attached to the catheter flash chamber, locking the retractable needle into position, substantially as previously described. The tubular sheath 9 has a constant internal diameter and the longitudinal slot 10 in the tubular sheath is open at the second end of the tubular sheath. The needle assembly is positioned in sheath 9 through the open end of sheath 9, with the pin 7(not shown in FIG. 29, for reasons of clarity) on the needle assembly entering the open end of slot 10 and slidably engaging the slot. A cover 307 fits over the second end of the tubular sheath and closes the longitudinal slot. The cover has an opening 308 which is large enough to allow the hollow needle to pass therethrough, but is too small to allow the hub of the needle assembly to pass therethrough. The cover has a skirt 309 that fits over the tubular sheath, said skirt having an external surface with a means for gripping the posterior end of the tubular sheath thereon. The gripping means may comprise two tabs 310 on opposing sides of the skirt.

When the retractable catheter needle is in its exposed position, a flexible catheter 111 having a longitudinal bore therethrough is supported by the needle 100 (FIG. 30). The tip of the needle is exposed through an opening at one end of the catheter. The other end of the catheter is adapted to fit over extension 110, reversibly securing the catheter in position. A knob or other gripping means 112 allows the user to grasp the catheter after it has been inserted into a patient. The needle may then be withdrawn from the catheter, with the catheter remaining in position in the patient. The needle is then retracted into the container. Normally, the catheter is initially provided in position on the needle, with a protective cap or sheath covering the needle and catheter.

Figure 31A:
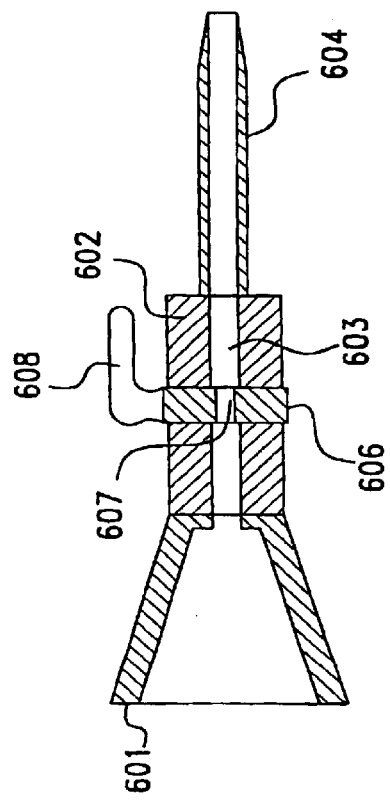
FIGS. 31a through 31d show a catheter adapted for use with the catheter assembly of claim 27, said catheter having a stopcock assembly.
Figure 31B:
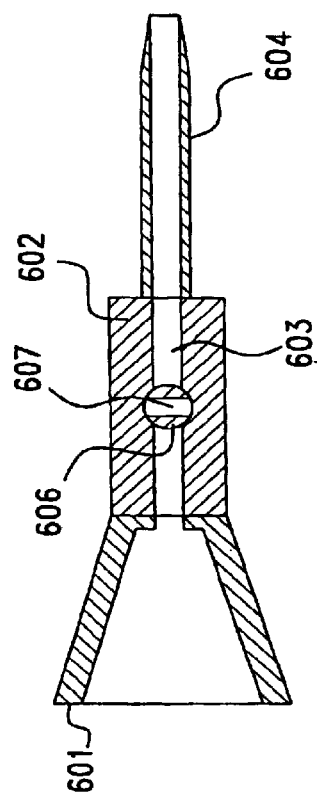
Figure 31C:
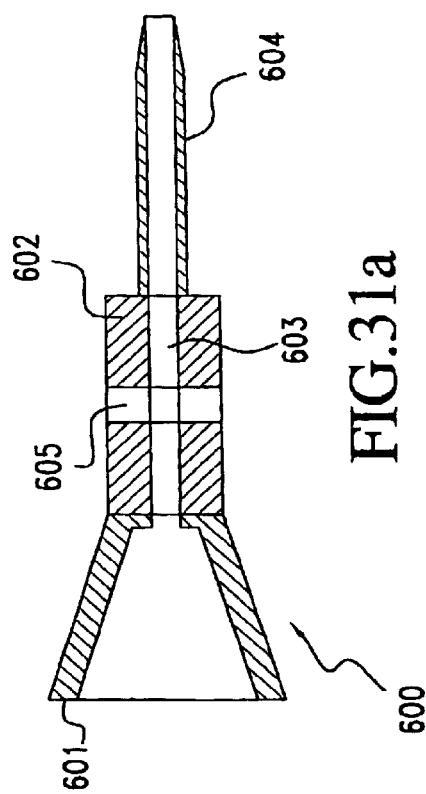
Figure 31D:
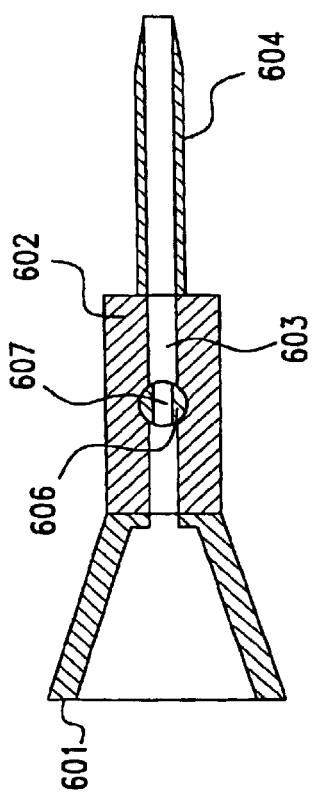

For those embodiments of the invention described herein which are intended for use with a catheter, it is now proposed to describe the catheter 600 intended for use with this invention (See FIGS. 31a and 31b). The preferred catheter 600 comprises a joint 601 adapted to fit onto a joint on the posterior end of the tubular sheath surrounding the needle assembly. The joint on the catheter may be a female joint adapted to frictionally engage a male joint on the tubular sheath, or the joint on the catheter may be adapted to engage a joint on the tubular sheath by means of a Luer-Loc® connection. The joint on the catheter is connected with a first end of a hub 602 having a longitudinal bore 603 therethrough. A second end of the hub is connected with a cannula 604 having a longitudinal bore therethrough, where the bore of the cannula is in fluid communication with the longitudinal bore of the hub. When the hub of the catheter is connected to the joint on the tubular sheath, the bore of the cannula is also in fluid communication with a longitudinal bore in the joint on the posterior end of the tubular sheath. The hub of the catheter additionally features a tranverse bore 605, which intersects the longitudinal bore therethrough. A stopcock 606 having a transverse bore 607 is fitted into the bore 605. A handle 608 on the stopcock allows the user to rotate the stopcock between a first open position (FIG. 31c), which allows the flow of fluid through bore 603, and a second closed position (FIG. 319) that blocks the flow of fluid through bore 603.

What is claimed is:

1. A retractable needle assembly for use in medical procedures, comprising:

a) a needle assembly, said needle assembly comprising a hub having an anterior end and a posterior end, a hollow needle passing through the hub and projecting from the posterior end of the hub; and a tubular sleeve connected with a peripheral edge of the hub and projecting from the anterior end of the hub, said sleeve having a radially directed hole therethrough;

b) a tubular sheath having a wall with a radially directed hole therethrough, an anterior end, and a posterior end, said posterior end having an opening therethrough, wherein the needle assembly is positioned within the tubular sheath with the hollow needle projecting from the posterior end of the hub being directed toward the opening in the posterior end of the sheath, wherein said needle assembly may be moved reversibly along an axis of the sheath between an exposed position in which the hollow needle passes through the opening in the posterior end of the sheath and a retracted position in which the hollow needle is contained within the tubular sheath, and wherein the opening in the posterior end of the sheath is large enough to allow the hollow needle to pass therethrough, but too small to allow the hub to pass therethrough;

c) a means for reversibly locking the needle assembly in its exposed position;

d) a means for reversibly locking the needle assembly in its retracted position; and e) a means for permanently locking the needle assembly in its retracted position, said permanent locking means comprising a radially-directed peg, said radially-directed peg being mounted on an exterior surface of the tubular sheath so that one end of the radially-directed peg is adapted to be pushed inwardly through the hole in the wall of the tubular sheath and through the hole in the tubular sleeve, wherein said one end of the radially-directed peg cannot be withdrawn through the hole in the tubular sleeve after it has been pushed through the hole in the tubular sleeve.

2. The retractable needle assembly of claim 1, wherein the means for permanently locking the needle assembly in its retracted position cannot be used unless the needle has first been reversibly locked in its retracted position.

3. The retractable needle assembly for use in medical procedures of claim 1, wherein the means for permanently locking the needle assembly in its retracted position further comprises a tubular mount connected with the external surface of the tubular sheath and a stop on the external surface of the radially-directed peg, said tubular mount having an inwardly projecting flange on an outer end thereof;

wherein the radially-directed peg is slidably mounted within the tubular mount; and wherein the flange on the tubular mount retains the stop on the external surface of the radially-directed peg within the tubular mount.

4. The retractable needle assembly for use in medical procedures of claim 1, wherein the radially directed peg has at least one flexible projection thereon, said flexible projection is adapted to bend as said one end of the radially-directed peg is pushed inwardly through the hole in the wall of the tubular sheath, but is unable to bend when an attempt to withdraw said one end of the radially-directed peg through the hole in the wall of the tubular sheath is made.

5. The retractable needle assembly for use in medical procedures of claim 1, wherein the radially directed peg has a flexible frustoconical tube attached thereto, said frustoconical tube having walls which are adapted to bend as said one end of the radially-directed peg is pushed inwardly through the hole in the tubular sleeve, but which are unable to bend when an attempt to withdraw said one end of the radially-directed peg through the hole in the tubular sleeve is made.

6. The retractable needle assembly for use in medical procedures of claim 1, wherein the radially directed peg has at least one rigid projection thereon, wherein said rigid projection is adapted to irreversibly penetrate the hole in the tubular sleeve when one end of the radially-directed peg is pushed inwardly therethrough.

7. The retractable needle assembly for use in medical procedures of claim 4 wherein the said needle assembly may be moved reversibly along an axis of the sheath by means of a radially projecting member rigidly connected with the hub of the needle assembly and a longitudinal slot through the wall of the tubular sheath, wherein the radially projecting member is slidably engaged by the longitudinal slot.

8. The retractable needle assembly of claim 7, wherein the means for reversibly locking the needle assembly in its exposed position comprises a first locking slot which intersects the longitudinal slot near the posterior end of the tubular sheath, said first locking slot being adapted to admit the radially projecting member.

9. The retractable needle assembly of claim 8, wherein the first locking slot is a straight slot, a curved slot, an L-shaped slot, a T-shaped slot, or a C-shaped slot.

10. The retractable needle assembly of claim 8, wherein the first locking slot is an L-shaped slot.

11. The retractable needle assembly of claim 8, wherein the first locking slot comprises a tooth near its entrance, wherein said tooth narrows the entrance to a width which is less than the width of the radially projecting member, but which is large enough to allow the radially projecting member to be pushed therethrough.

12. The retractable needle assembly of claim 7, wherein the means for reversibly locking the needle assembly in its retracted position comprises a second locking slot which intersects the longitudinal slot near the anterior end of the tubular sheath, said second locking slot being adapted to admit the radially projecting member.

13. The retractable needle assembly of claim 12, wherein the second locking slot is a straight slot or an L-shaped slot.

14. The retractable needle assembly of claim 12, wherein the second locking slot is a straight slot.

15. The retractable needle assembly of claim 12, wherein the radially directed hole through the tubular sleeve and the radially directed hole through the tubular sheath are aligned only when the radially projecting member enters the second locking slot.

16. The retractable needle assembly of claim 12, wherein the second locking slot comprises a tooth near its entrance, wherein said tooth narrows the entrance to a width which is less than the width of the radially projecting member, but which is large enough to allow the radially projecting member to be pushed therethrough.

17. The retractable needle assembly of claim 7, wherein the means for reversibly locking the needle assembly in its exposed position comprises a first locking slot which intersects the longitudinal slot near the posterior end of the tubular sheath, and the means for reversibly locking the needle assembly in its retracted position comprises a second locking slot which intersects the longitudinal slot near the anterior end of the tubular sheath, said first and second locking slots being adapted to admit the radially projecting member.

18. The apparatus of claim 7, wherein the means for reversibly locking the needle assembly in its exposed position comprises a pair of teeth on opposite sides of the longitudinal slot, said pair of teeth being positioned near a posterior end of the tubular sheath, wherein a locking position is defined between the teeth and the posterior end of the longitudinal slot; and wherein the teeth cause the width of the slot to narrow to a width which is smaller than the diameter of the radially projecting member, but large enough to allow a user to push the radially projecting member through the teeth.

19. The apparatus of claim 7, wherein the means for reversibly locking the needle assembly in its retracted position comprises a pair of teeth on opposite sides of the longitudinal slot, said pair of teeth being positioned near an anterior end of the tubular sheath, wherein a locking position is defined between the teeth and the anterior end of the longitudinal slot; and wherein the teeth cause the width of the slot to narrow to a width which is smaller than the diameter of the radially projecting member, but large enough to allow a user to push the radially projecting member through the teeth.

20. The retractable needle assembly of claim 7, wherein the means for reversibly locking the needle assembly in its exposed position comprises a first hook which engages the radially projecting member, and the means for reversibly locking the needle assembly in its retracted position comprises a second hook which engages the radially projecting member, wherein the first hook is located at the posterior end of the longitudinal slot and the second hook is located at the anterior end of the longitudinal slot.

21. The retractable needle assembly of claim 7, wherein one end of the radially projecting member is exposed through the longitudinal slot, and a thumbrest is attached to said one end of said radially projecting member.

22. The retractable needle assembly of claim 1, wherein the longitudinal slot in the tubular sheath is open at a first end of the tubular sheath, and closed at the other end of the tubular sheath; and wherein a separate element is secured to the exterior surface of the first end of the tubular sheath to close the open end of the longitudinal slot.

23. The retractable needle assembly of claim 22, wherein the longitudinal slot in the tubular sheath is open at the anterior end of the tubular sheath; and wherein the separate element is a ring having a radially-directed hole therethrough, that fits over the exterior surface of the anterior end of the tubular sheath, an exterior surface of said ring having a radially projecting cylinder thereon, said radially projecting cylinder having a bore therethrough, said bore in said radially projecting cylinder being aligned with said radially directed hole in said ring and said radially directed hole in said tubular sheath;

wherein said radially directed peg is slidably positioned within the bore of said radially projecting cylinder.

24. The retractable needle assembly of claim 23, wherein the ring closes the open end of the longitudinal slot while leaving an opening at the anterior end of the tubular sheath.

25. The retractable needle assembly of claim 23, further comprising a catheter;

wherein the needle assembly is in its exposed position and the catheter is releasably supported by the hollow needle;

wherein the anterior end of the tubular sheath is closed; and wherein the means for reversibly locking the needle assembly in its exposed position comprises a first locking slot which intersects the longitudinal slot near the posterior end of the tubular sheath, said first locking slot being adapted to admit the radially projecting member, wherein the first locking slot is an L-shaped slot.

26. The retractable needle assembly of claim 25, wherein the catheter comprises:

a) a female joint;
b) a catheter hub having a longitudinal bore therethrough, said catheter hub being connected with the female joint;
c) a cannula having a longitudinal bore therethrough, where the bore of the cannula is in fluid communication with the longitudinal bore of the catheter hub; and
d) a stopcock having a transverse bore therethrough; and
e) a stopcock handle;
wherein the catheter hub additionally features a tranverse bore which intersects the longitudinal bore therethrough, said stopcock being mounted within the transverse bore of the catheter hub;
wherein the stopcock handle is adapted to allow the user to reversibly rotate the stopcock between a first open position which allows the flow of fluid through the longitudinal bore of the catheter hub, and a second closed position which blocks the flow of fluid through the longitudinal bore of the catheter hub.

27. The retractable needle assembly of claim 22, wherein the tubular sheath has a constant internal diameter and the longitudinal slot in the tubular sheath is open at the posterior end of the tubular sheath; and wherein the separate element is a cover that fits over the posterior end of the tubular sheath, said cover having an opening which is large enough to allow the hollow needle to pass therethrough, but too small to allow the hub to pass therethrough.

28. The retractable needle assembly of claim 27, wherein the cover has a skirt that fits over the posterior end of the tubular sheath, said skirt having an external surface with a means for gripping the posterior end of the tubular sheath thereon.

29. The retractable needle assembly of claim 27, wherein an exterior surface of said tubular sheath has a radially projecting cylinder thereon, said radially projecting cylinder having a bore therethrough, said bore in said radially projecting cylinder being aligned with said radially directed hole in said tubular sheath;

wherein said radially directed peg is slidably positioned within the bore of said radially projecting cylinder.

30. The retractable needle assembly of claim 7, wherein the anterior end of the tubular sheath has an opening which is adapted to admit a syringe barrel, and an interior surface of the tubular sleeve defines a cavity which is adapted to engage a male joint on the syringe barrel, where a longitudinal bore through the male joint places an interior of the hollow needle in fluid communication with an interior of the syringe barrel.

31. The retractable needle assembly of claim 30, wherein the tubular sleeve is adapted to:

frictionally engage a male joint on the syringe barrel;
engage a threaded joint on the syringe barrel; or
engage a Luer-Loc connector on the syringe barrel.

32. The retractable needle assembly of claim 7, wherein the anterior end of the tubular sheath has an opening which is adapted to admit an evacuated test tube sealed with a rubber septum, and wherein the hollow needle passing through the hub has a first end which projects from the posterior end of the hub and a second end which projects from the anterior end of the hub, said second end of the needle being adapted to penetrate said rubber septum so that an interior of the hollow needle is in fluid communication with an interior of the evacuated tube.

33. The retractable needle assembly of claim 7, wherein the needle assembly comprises a hub having an anterior end and a posterior end; a hollow needle passing through the hub and projecting from the posterior end of the hub; a flash chamber having an anterior end and a posterior end which is connected with the anterior end of the hub, an interior of said flash chamber being in fluid communication with an interior of the hollow needle; and a tubular sleeve connected with the anterior end of the flash chamber, said sleeve having a radially directed hole therethrough.

34. The retractable needle assembly of claim 33, further comprising a catheter, and a catheter engaging means on the posterior end of the tubular sheath;

wherein the needle assembly is initially in its exposed position;

wherein the catheter is supported by the hollow needle; and wherein the catheter is releasably engaged by the catheter engaging means on the tubular sheath.

35. The retractable needle assembly of claim 33, further comprising a pair of finger grips on opposite sides of the tubular sheath, with the longitudinal slot being positioned between the finger grips.

36. The retractable needle assembly of claim 7, wherein the needle assembly further comprises a female joint rigidly connected with the anterior end of the tubular sheath, and an adjustable-length tube connecting the female joint with the anterior end of the hub of the needle assembly, said adjustable-length tube being reversibly adjustable between an extended configuration and a contracted configuration;

wherein when the adjustable-length tube is in its contracted configuration, the needle assembly is in its retracted position, and when the adjustable-length tube is in its extended configuration, the needle assembly is in its exposed position; and wherein the female joint is adapted to frictionally engage the tip of a syringe barrel, so as to place an interior of said syringe barrel in fluid communication with an interior of the adjustable-length tube and an interior of the hollow needle.

37. The retractable needle assembly of claim 36, wherein the tubular sleeve is coaxial with the adjustable-length tube.

38. The retractable needle assembly of claim 36, wherein the adjustable-length tube is connected to the tubular sheath by a collar ring which comprises an outer skirt which fits over an outer surface of the tubular sheath, the outer skirt being connected with an inner skirt which fits inside the tubular sheath;

wherein the female joint is rigidly connected with the inner skirt of the collar ring.

39. The retractable needle assembly of claim 36, wherein the tubular sleeve surrounds the end of the adjustable-length tube which is connected to the anterior end of the hub of the needle assembly.

40. The retractable needle assembly of claim 36, wherein the adjustable-length tube has corrugated walls which are collapsible.

41. The retractable needle assembly of claim 36, wherein the adjustable-length tube is made from an inner tube and an outer tube, wherein the inner tube is movable in an axial direction, relative to the outer tube.

42. The retractable needle assembly of claim 7, wherein the radially projecting member has a circular cross section.

43. The retractable needle assembly of claim 7, wherein the radially projecting member has a non-circular cross-section.

44. The retractable needle assembly of claim 7, wherein the radially projecting member has a cross section selected from the group consisting of an oval cross section, a square cross section, or a rectangular cross section.

45. The retractable needle assembly of claim 7, further comprising a means for reversibly biasing the needle assembly into its retracted position.

46. The retractable needle assembly of claim 45, wherein the reversible biasing means is a spring.

* * * * *